(12) United States Patent
Schmidt et al.

(10) Patent No.: US 8,263,806 B2
(45) Date of Patent: Sep. 11, 2012

(54) METHOD FOR PRODUCING SULFONAMIDES

(75) Inventors: Thomas Schmidt, Neustadt (DE); Joachim Gebhardt, Wachenheim (DE); Sandra Löhr, Ludwigshafen (DE); Michael Keil, Freinsheim (DE); Jan Hendrik Wevers, Hohensülzen (DE); Michael Rack, Eppelheim (DE); Guido Mayer, Gönnheim (DE); Axel Pleschke, Mannheim (DE)

(73) Assignee: BASF SE, Ludwigshafen (DE)

( * ) Notice: Subject to any disclaimer, the term of this patent is extended or adjusted under 35 U.S.C. 154(b) by 992 days.

(21) Appl. No.: 12/095,582

(22) PCT Filed: Nov. 23, 2006

(86) PCT No.: PCT/EP2006/068832
§ 371 (c)(1),
(2), (4) Date: May 30, 2008

(87) PCT Pub. No.: WO2007/063028
PCT Pub. Date: Jun. 7, 2007

(65) Prior Publication Data
US 2010/0228054 A1  Sep. 9, 2010

(30) Foreign Application Priority Data

Dec. 1, 2005 (DE) .................... 10 2005 057 681
Nov. 7, 2006 (EP) ..................... 06123569

(51) Int. Cl.
*C07C 381/00* (2006.01)

(52) U.S. Cl. ............................................. 564/79
(58) Field of Classification Search .......... 564/79
See application file for complete search history.

(56) References Cited

U.S. PATENT DOCUMENTS

| | | | |
|---|---|---|---|
| 3,198,785 | A | 8/1965 | Houlihan |
| 5,017,211 | A | 5/1991 | Wenger et al. |
| 5,238,908 | A | 8/1993 | Lange et al. |
| 6,251,829 | B1 | 6/2001 | Li et al. |
| 2005/0159622 | A1 | 7/2005 | Hamprecht et al. |
| 2006/0004220 | A1 | 1/2006 | Hamprecht et al. |
| 2008/0033174 | A1 | 2/2008 | Lohr et al. |
| 2010/0222586 | A1 | 9/2010 | Pleschke et al. |
| 2010/0228054 | A1 | 9/2010 | Keil et al. |

FOREIGN PATENT DOCUMENTS

| | | |
|---|---|---|
| DE | 1240853 | 5/1967 |
| WO | WO 89/02891 | 4/1989 |
| WO | WO 01/83459 | 11/2001 |
| WO | WO 03/097589 | 11/2003 |
| WO | WO 2004/035545 | 4/2004 |
| WO | WO 2004/039768 | 5/2004 |
| WO | WO 2004/106324 | 12/2004 |
| WO | WO 2006/010474 | 2/2006 |
| WO | WO 2006/090210 | 8/2006 |
| WO | WO 2007063028 | 6/2007 |
| WO | WO 2009/050120 | 4/2009 |

OTHER PUBLICATIONS

International Search Report for International Application No. PCT/EP2006/068832, International Filing Date, Nov. 23, 2006.
Beckert, R. et al., "Elecktrophile aromatische substitution", Organikum, 22$^{nd}$ ed., 358-361 (2004).
Beckert, R. et al., "Reaktionen von Carbonylverbindungen", Organikum, 22$^{nd}$ ed., 496-499 (2004).
Hamprecht, Von Gerhard et al., "Alkylsulfamidsäurechloride als Schlüsselbausteine für neue Pflanzenschutzwirkstoffe", Agnew. Chem. 93, 151-163 (1981).
Unterhalt, B., "Schwefelsäure-di-N-Derivate", in Methoden der organischen Chemie [Methods of organic chemistry], Houben-Weyl ed., E11, p. 1019-1025 (1985).
Scherer, O. et al., "Reaktionen mit benzotrichlorid und pentacholoräthyl-benzol", Justus Liebigs Annalen der Chemie, vol. 677, p. 83-95 (1964).
International Preliminary Report on Patentability for International Application No. PCT/EP2006/068832; International Filing Date: Nov. 23, 2006; Date of Submission: Sep. 28, 2007; Date of Completion: May 15, 2008.
Adkison et al., "Semicarbazone-Based Inhibitors of Cathepsin K, Are They Prodrugs for Aldehyde Inhibitors," Bioorganic and Medicinal Chemistry Letters, vol. 16, No. 4, (2006), pp. 978-983. XP002474074.
Audrieth et al., "Hydrazides of Sulfuric Acid and Their Derivatives. II. The Sulfamyl Hydrazides," J. Org. Chem., vol. 21, No. 4, (1956), pp. 426-428. XP002474073.
Behrend, "Über die Einwirkung von Sulfurylchlorid auf secundäre Aminbasen," Justus Liebigs Annalen Der Chemie, vol. 222, (1884), pp. 116-136. XP002474075.
Binkley ed Degering, "Organic Synthesis with Sulfuryl Chloride," J. Am. Chem. Soc., vol. 61, (1939), pp. 3250-3251. XP002474072.
Vandi et al., "Synthesis and Properties of Some N-Substituted Sulfamides," J. Org. Chem., vol. 26, No. 4, (1961), pp. 1136-1138. XP002474071.
Wheeler et al., "Preparation and Properties of Certain Derivatives of Sulfamide," J. Am. Chem. Soc., vol. 66, (1944), pp. 1242-1243.

*Primary Examiner* — Peter G O Sullivan
(74) *Attorney, Agent, or Firm* — Brinks Hofer Gilson & Lione

(57) ABSTRACT

The invention relates to methods for producing sulfonamides of formula I, wherein the variables have the designations cited in the description, by reacting m-nitro-benzoic acid chlorides of formula II with aminosulfons of formula III, under the influence of B equivalents of base IV. Said method is characterized in that, during step a) the aminosulfon of formula III is reacted with B1 equivalents of base IV, and during step b), the reaction mixture resulting from step a) is reacted with m-nitro-benzoic acid chlorides of formula II and B2 equivalents of base IV; B, B1 and B2 having the designations cited in the description.

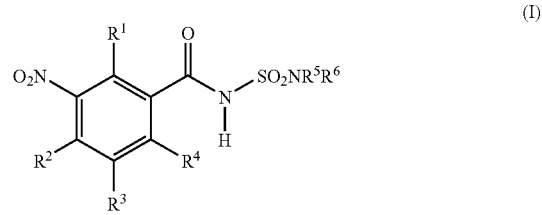

(I)

19 Claims, No Drawings

METHOD FOR PRODUCING SULFONAMIDES

This application is a National Stage application of International Application No. PCT/EP2006/068832 filed Nov. 23, 2006, the entire contents of which is hereby incorporated herein by reference. This application also claims the benefit under 35 U.S.C. §119 of German Patent Application No. 10 2005 057 681.8, filed Dec. 1, 2005, and European Patent Application No. 06123569.3, filed Nov. 7, 2006, the entire contents of which is hereby incorporated herein by reference.

The present invention relates to a process for preparing sulfonamides I

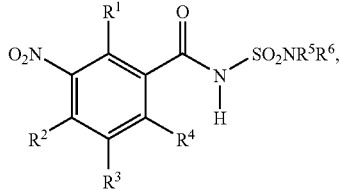

where the variables are each defined as follows:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
$R^5$ and $R^6$ are hydrogen, $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_6$-alkoxy, phenyl or benzyl.

In the prior art, for example in WO 01/83459, a process is described for preparing heterocyclyl-substituted phenylsulfamoylcarboxamides by the reaction of benzoic acid derivatives with sulfamides in the presence if appropriate of a coupling reagent.

Moreover it is known for example from WO 04/39768 that N-aroylsulfonamides can be prepared by the reaction of corresponding benzoic acid derivatives with sulfonic diamides under the influence of base, by initially introducing sulfonic diamides and the base and then adding the benzoic acid derivative.

It is thus an object of the present invention to provide a simple, economically viable and implementable process for preparing sulfonamides I, which firstly distinctly reduces byproduct formation and simultaneously can achieve high yields and high purity of product of value.

We have found that, surprisingly, this object is achieved by a process in which m-nitrobenzoyl chlorides II are reacted with amino sulfones III under the influence of 1.5 to 3 equivalents of base IV based on the amino sulfone III, which comprises, in step a), reacting the amino sulfone III with 0.1-1.3 equivalents of base IV, and, in step b), reacting the reaction mixture resulting from step a) with m-nitrobenzoyl chlorides II and the remaining portion of base IV.

Accordingly, the present invention relates to a process for preparing sulfonamides I

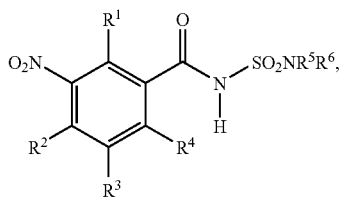

where the variables are each defined as follows:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
$R^5$ and $R^6$ are each hydrogen, $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_6$-alkoxy, phenyl or benzyl;
by reacting m-nitrobenzoyl chlorides II

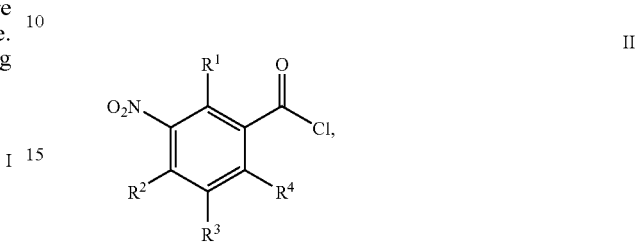

where the variables $R^1$, $R^2$, $R^3$ and $R^4$ are each as defined above;
with amino sulfones III

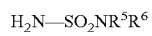

$H_2N$—$SO_2NR^5R^6$   III, where the variables $R^5$ and $R^6$ are each as defined above;
under the influence of B equivalents of base IV, wherein, in step a), the amino sulfone III is reacted with B1 equivalents of base IV, and, in step b), the reaction mixture resulting from step a) is reacted with m-nitrobenzoyl chloride II and B2 equivalents of base IV;
where
 B is 1.5-3 equivalents of base IV with respect to the amino sulfone III;
 B1 is a subportion of B and is in the range from 0.1-1.3 equivalents of base IV with respect to the amino sulfone III; and
 B2 is a subportion of B and is the difference between B and B1.

Depending on the substitution pattern, the sulfonamides I prepared by the process according to the invention may comprise one or more centers of chirality and are then present in the form of an enantiomeric or diastereomeric mixtures. The invention thus provides a process for preparing either the pure enantiomers or diastereomers, or their mixtures.

The organic molecular moieties specified for the substituents $R^1$ to $R^6$ and $R^a$, $R^b$ and $R^c$ constitute collective terms for individual lists of the individual group members. All hydrocarbon chains, i.e. all alkyl, haloalkyl, alkoxy and haloalkoxy moieties, may be straight-chain or branched.

Unless stated otherwise, halogenated substituents preferably bear from one to five identical or different halogen atoms. The term halogen in each case represents fluorine, chlorine, bromine or iodine.

Examples of definitions include:
 $C_1$-$C_4$-alkyl: for example methyl, ethyl, n-propyl, 1-methylethyl, n-butyl, 1-methylpropyl, 2-methylpropyl and 1,1-dimethylethyl;
 $C_1$-$C_6$-alkyl: $C_1$-$C_4$-alkyl as specified above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$-$C_4$-haloalkyl: a $C_1$-$C_4$-alkyl radical as specified above which is partly or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloro-propyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$-$C_6$-haloalkyl: $C_1$-$C_4$-haloalkyl as specified above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and tridecafluorohexyl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkynyl: for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_8$-cycloalkyl: for example cyclopropyl, cyclobutyl, cyclopentyl, cyclohexyl and cycloheptyl;

$C_3$-$C_7$-cycloalkenyl: for example 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl; 1-cycloheptenyl, 3-cycloheptenyl, 4-cycloheptenyl, 3,5-cycloheptadienyl, 2,4-cycloheptadienyl, 1,3-cycloheptadienyl, 1,3,5-cycloheptatrienyl, 2,4,6-cycloheptatrienyl;

$C_1$-$C_4$-alkoxy: for example methoxy, ethoxy, propoxy, 1-methylethoxy, butoxy, 1-methylpropoxy, 2-methylpropoxy and 1,1-dimethylethoxy;

$C_1$-$C_6$-alkoxy: $C_1$-$C_4$-alkoxy as specified above, and also, for example, pentoxy, 1-methylbutoxy, 2-methylbutoxy, 3-methoxybutoxy, 1,1-dimethylpropoxy, 1,2-di-methylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-tri-methylpropoxy, 1-ethyl-1-methylpropoxy and 1-ethyl-2-methylpropoxy;

$C_1$-$C_4$-haloalkoxy: a $C_1$-$C_4$-alkoxy radical as specified above which is partly or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy: $C_1$-$C_4$-haloalkoxy as specified above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and tridecafluorohexoxy.

In particularly preferred embodiments of the process according to the invention, the variables $R^1$, $R^2$, $R^3$, $R^4$, $R^5$ and $R^6$ are each defined as follows, these definitions, alone and also in combination with one another, constituting particular embodiments of the process according to the invention:

Preference is given to the embodiment of the process according to the invention in which
$R^1$ is hydrogen, halogen or $C_1$-$C_6$-alkyl;
preferably hydrogen or halogen;
very preferably hydrogen, fluorine or chlorine;
more preferably hydrogen.

Equally preferred is the embodiment of the process according to the invention in which
$R^2$ is hydrogen, halogen, cyano, $C_1$-$C_6$-alkyl or $C_1$-$C_6$-haloalkyl;
preferably hydrogen or halogen;
very preferably hydrogen, fluorine or chlorine;

more preferably hydrogen or fluorine;
exceptionally preferably hydrogen;
equally exceptionally preferably fluorine.
Equally preferred is the embodiment of the process according to the invention in which
$R^2$ is hydrogen or halogen;
preferably halogen;
very preferably fluorine or chlorine;
more preferably fluorine.
Equally preferred is the embodiment of the process according to the invention in which
$R^3$ is hydrogen, halogen or $C_1$-$C_6$-alkyl;
preferably hydrogen or halogen;
very preferably hydrogen, fluorine or chlorine;
more preferably hydrogen.
Equally preferred is the embodiment of the process according to the invention in which
$R^4$ is hydrogen, halogen, cyano, $C_1$-$C_6$-alkyl or $C_1$-$C_6$-haloalkyl;
preferably hydrogen, halogen or cyano;
very preferably hydrogen, fluorine, chlorine or cyano;
more preferably hydrogen, chlorine or cyano;
exceptionally preferably hydrogen;
equally exceptionally preferably chlorine or cyano;
very exceptionally preferably chlorine.
Equally preferred is the embodiment of the process according to the invention in which
$R^4$ is halogen or cyano;
preferably halogen;
very preferably fluorine or chlorine; more preferably chlorine.
Equally preferred is the embodiment of the process according to the invention in which
$R^4$ is hydrogen, halogen or cyano;
preferably hydrogen or halogen;
very preferably hydrogen, fluorine or chlorine;
more preferably hydrogen or chlorine.
Equally preferred is the embodiment of the process according to the invention in which
$R^5$ and $R^6$ independently
are each hydrogen, $C_1$-$C_6$-alkyl or $C_2$-$C_6$-alkenyl;
preferably hydrogen or $C_1$-$C_6$-alkyl;
very preferably $C_1$-$C_6$-alkyl; more preferably $C_1$-$C_4$-alkyl.
Equally preferred is the embodiment of the process according to the invention in which
$R^5$ is hydrogen or $C_1$-$C_6$-alkyl;
preferably hydrogen or $C_1$-$C_4$-alkyl;
very preferably $C_1$-$C_4$-alkyl;
more preferably methyl.
Equally preferred is the embodiment of the process according to the invention in which
$R^6$ is hydrogen or $C_1$-$C_6$-alkyl;
preferably hydrogen or $C_1$-$C_4$-alkyl;
very preferably $C_1$-$C_4$-alkyl.
In a very preferred embodiment of the process according to the invention, the variables $R^1$, $R^2$, $R^3$ and $R^4$ are each as defined above, in particular the meanings indicated as preferred, where at least one of the radicals $R^1$ to $R^4$ is fluorine.
In a further very preferred embodiment of the process according to the invention, the variables $R^1$, $R^2$, $R^3$ and $R^4$ are each defined as follows:
$R^1$ is hydrogen;
$R^2$ is hydrogen or halogen;
preferably halogen;
very preferably fluorine;
$R^3$ is hydrogen; and
$R^4$ is hydrogen, chlorine or cyano;

preferably chlorine or cyano;
very preferably chlorine.
In a further very preferred embodiment of the process according to the invention, the variables $R^1$, $R^2$, $R^3$ and $R^4$ are each defined as follows:
$R^1$ is hydrogen;
$R^2$ is hydrogen or halogen;
preferably halogen;
very preferably fluorine;
$R^3$ is hydrogen; and
$R^4$ is hydrogen or halogen;
preferably hydrogen or chlorine;
very preferably chlorine;
equally very preferably hydrogen.
In a further very preferred embodiment of the process according to the invention, the variables $R^1$, $R^2$, $R^3$ and $R^4$ are each defined as follows:
$R^1$ is hydrogen;
$R^2$ is fluorine;
$R^3$ is hydrogen; and
$R^4$ is halogen;
preferably chlorine.
In a further very preferred embodiment of the process according to the invention, the variables $R^1$, $R^2$, $R^3$, $R^4$ and $R^5$ are each defined as follows:
$R^1$ is hydrogen;
$R^2$ is hydrogen or halogen;
preferably halogen;
very preferably fluorine;
$R^3$ is hydrogen; and
$R^4$ is hydrogen or halogen;
preferably hydrogen or chlorine;
very preferably chlorine;
equally very preferably hydrogen;
$R^5$ and $R^6$ are each hydrogen, $C_1$-$C_6$-alkyl or $C_2$-$C_6$-alkenyl;
preferably hydrogen or $C_1$-$C_6$-alkyl;
very preferably $C_1$-$C_6$-alkyl;
more preferably $C_1$-$C_4$-alkyl.
In a preferred embodiment of the process according to the invention, it is possible in this way to prepare sulfonamides IA

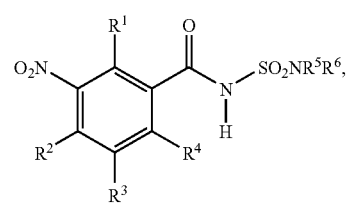

where the variables are each as defined below:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy; and
where at least one of the radicals $R^1$ to $R^4$ is fluorine, and
$R^5$ and $R^6$ are each hydrogen, $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_6$-alkoxy, phenyl or benzyl.

In a further preferred embodiment of the process according to the invention, it is possible in this way to prepare sulfonamides I.a

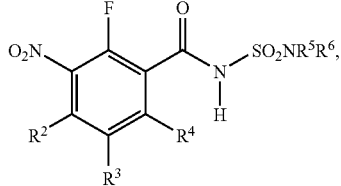

where the variables $R^2$, $R^3$, $R^4$, $R^5$ and $R^6$ are each as defined above, especially as defined above with preference.

In a further preferred embodiment of the process according to the invention, it is possible in this way to prepare sulfonamides I.b

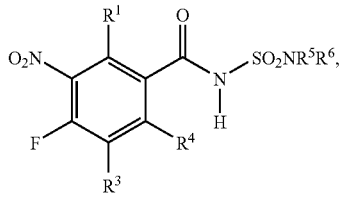

where the variables $R^1$, $R^3$, $R^4$, $R^5$ and $R^6$ are each as defined above, especially as defined above with preference.

In a further preferred embodiment of the process according to the invention, it is possible in this way to prepare sulfonamides I.c

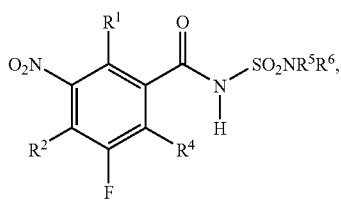

where the variables $R^1$, $R^2$, $R^4$, $R^5$ and $R^6$ are each as defined above, especially as defined above with preference.

In a further preferred embodiment of the process according to the invention, it is possible in this way to prepare sulfonamides I.d

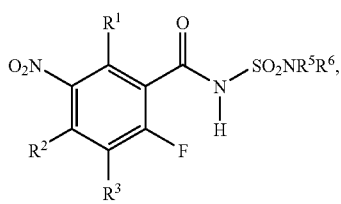

where the variables $R^1$, $R^2$, $R^3$, $R^5$ and $R^6$ are each as defined above, especially as defined above with preference.

In a further preferred embodiment of the process according to the invention, it is possible in this way to prepare sulfonamides I.e

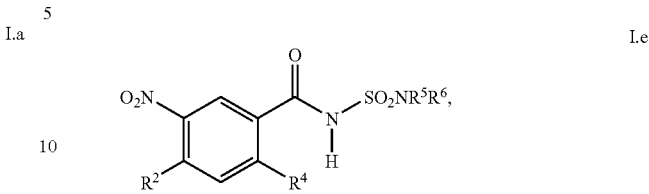

where the variables $R^2$, $R^4$, $R^5$ and $R^6$ are each as defined above, especially as defined above with preference, and where at least one of the $R^2$ and $R^4$ radicals is fluorine.

Outlined below are the preferred embodiments of the process according to the invention, which, both considered on their own and considered in combination with one another, constitute special embodiments of the process according to the invention.

The m-nitrobenzoyl chlorides II and with amino sulfones III can be reacted in equimolar amounts with one another.

The molar amounts in which m-nitrobenzoyl chlorides II, preferably fluorinated m-nitrobenzoyl chlorides IIA, and amino sulfones III are reacted with one another are advantageously 1:0.9-1.8; preferably 1:0.9-1.5; very preferably 1:0.9-1.2; with particular preference 1:0.95-1.2; with extraordinary preference 1:0.95-1.1 for the ratio of II, preferably IIA, to III.

The reaction according to the invention of the m-nitrobenzoyl chlorides II with amino sulfones III to give sulfonamides I proceeds typically at temperatures of from −30° C. to 120° C., preferably from −10° C. to 100° C., especially preferably from 0° C. to 80° C., in an inert organic solvent under the influence of 1.5-3 equivalents of a base IV with respect to the amino sulfone III and, if appropriate, in the presence of a catalyst:

Suitable solvents are aliphatic hydrocarbons such as pentane, hexane, heptane, cyclohexane and mixtures of $C_5$-$C_8$-alkanes, aromatic hydrocarbons such as toluene, o-, m- and p-xylene, halogenated hydrocarbons such as methylene chloride, chloroform, dichloroethane and chlorobenzene, ethers such as diethyl ether, diisopropyl ether, tert-butyl methyl ether, dioxane, anisol and tetrahydrofuran, esters such as ethyl acetate, propyl acetate, n-butyl acetate, methyl isobutyrate, isobutyl acetate; and also dimethyl sulfoxide, dimethylformamide and dimethylacetamide; more preferably aromatic hydrocarbons and halogenated hydrocarbons.

It is also possible to use mixtures of the solvents mentioned, or mixtures of the solvents mentioned with water.

The inventive reaction of the m-nitrobenzoyl chlorides II with amino sulfones III to sulfonamides I takes place in the presence of a total of 1.5-3 equivalents of base IV with respect to the amino sulfone III. These 1.5-3 equivalents of base IV represent the total amount of base, "B", which is used in the process according to the invention.

In step a) of the process according to the invention the amino sulfone III is reacted with 0.1-1.3 equivalents of base with respect to the amino sulfone III. These 0.1-1.3 equivalents of base IV are a subportion of the aforementioned total amount of base, B and are also referred to as amount of base "B1".

In step b) of the process according to the invention the reaction mixture resulting from step a) is reacted with m-nitrobenzoyl chloride II and with the remaining amount of the total amount of base, B, minus B1. The remaining amount of the total amount of base B is also referred to as amount of base "B2".

Accordingly the relation between B, B1 and B2 is as follows: B1+B2=B.

Useful bases IV generally include inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, potassium carbonate and calcium carbonate, and alkali metal hydrogencarbonates such as sodium hydrogencarbonate, alkali metal and alkaline earth metal alkoxides such as sodium methoxide, sodium epoxide, potassium ethoxide, potassium tert-butoxide, potassium tert-pentoxide and dimethoxymagnesium, and also organic bases, for example tertiary amines such as trimethylamine, triethylamine, diisopropylethylamine and N-methylpiperidine, pyridine, substituted pyridines such as collidine, lutidine and 4-dimethylaminopyridine, and also bicyclic amines, for example 1,8-diazabicyclo[5.4.0]undec-7-ene (DBU) and 1,5-diazabicyclo[4.3.0]non-5-ene (DBN).

Particular preference is given to alkali metal and alkaline earth metal oxides and tertiary amines.

Particular preference given to alkali metal and alkaline earth metal hydroxides, extraordinary preference to alkali metal hydroxides.

1.5-3 equivalents of base IV (total amount of base B) are used, based on the amino sulfone III.

Very preferably B is 1.8-2.5 equivalents based on the amino sulfone III.

Great preference is also given to 1.8-2.5 equivalents, based on the m-nitrobenzoyl chlorides II, with particular preference on the fluorinated m-nitrobenzoyl chlorides IIA

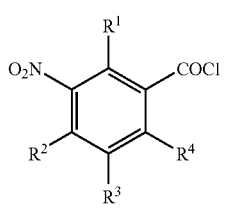

IIA where the variables are each defined as follows:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
and at least one of the radicals $R^1$ to $R^4$ is fluorine.

In step a) of the process according to the invention the amino sulfone III is preferably introduced initially in an inert solvent. Subsequently B1 equivalents of the base IV, i.e., 0.1-1.3 equivalents, preferably 0.1-1 equivalent, very preferably 0.2-0.95 equivalent of base IV are added. With particular advantage the base IV is added over a certain period of time. Very preferably the B1 equivalents of the base IV are added continuously, with very particular preference uniformly and continuously over a certain period of time.

This time period of the addition of the B1 equivalents of base IV in step a) can be from 1 minute up to 20 hours. More generally this time period is 1 minute to 6 hours, preferably 1 minute to 3 hours.

Alternatively, preferably in accordance with the variants described above, the amino sulfone III can be added to the desired amount of base I, more particularly to the amount of base B1 specified as being preferred.

In step b) of the process according to the invention, preferably, the m-nitrobenzoyl chloride II, preferably the fluorinated m-nitrobenzoyl chloride IIA, preferably in dilution in an inert solvent, and also the B2 equivalents of base IV are added to the reaction mixture resulting from step a), preferably likewise in dilution in an inert solvent. In step b), preferably, the addition of the m-nitrobenzoyl chloride II and also of the B2 equivalents of base IV take place simultaneously (i.e. parallel addition), very preferably simultaneously over a certain period of time, with particular preference simultaneously and continuously over a certain period of time, with very particular preference simultaneously and uniformly and continuously over a certain period of time, to the reaction mixture resulting from step a).

This time period for the addition of the m-nitrobenzoyl chloride II and also of the B2 equivalents of base IV in step b) can be from 1 minute up to 20 hours. More generally this time period is 1 minute to 6 hours, preferably 1 minute to 3 hours.

Alternatively, preferably in accordance with the variants described above, the reaction mixture resulting from step a) and also the amount of base B2 can be added simultaneously, preferably offset over a certain period of time, to the m-nitrobenzoyl chloride II, preferably in dilution in an inert solvent.

Furthermore, the m-nitrobenzoyl chloride II, preferably the fluorinated m-nitrobenzoyl chloride IIA, can also be reacted in bulk, i.e., e.g., in the form of its melt, with the amino sulfone III, in which case III is preferably dissolved in an inert solvent, the reaction taking place under the influence of a base, preferably as described above.

In a further variant of the process according to the invention the reaction can also be carried out in an aqueous multiphase system. This variant is preferred.

In another variant of the process according to the invention, the reaction can also be carried out in an aqueous multiphase system with and without phase transfer catalyst (PTC).

Preference is given to effecting the reaction in an aqueous multiphase system in the presence of phase transfer catalysts.

Preference is given to effecting the reaction in an aqueous multiphase system in the presence of phase transfer catalysts such as quaternary ammonium salts, phosphonium salts, polyglycols and crown ethers.

Suitable quaternary ammonium salts comprise
tetra($C_1$-$C_{18}$)alkylammonium fluorides, chlorides, bromides, iodides, hydrogensulfates, hydroxides, perchlorates, borates, diborates or tetrafluoroborates, such as tetramethyl ammonium fluoride tetrahydrate, tetramethylammonium chloride, tetramethylammonium bromide, tetramethylammonium iodide, tetramethylammonium hydroxide, methyltributylammonium chloride (e.g. ALIQUAT® 175), methyltrioctylammonium chloride, methyltricaprylylammonium chloride (e.g. ALIQUAT® 336, ALIQUAT® HTA1), tetraethylammonium chloride, tetraethylammonium chloride hydrate, tetraethylammonium bromide, tetraethylammonium hydroxide, tetrabutylammonium fluoride, tetrabutylammonium fluoride trihydrate, tetrabutylammonium chloride, tetrabutylammonium bromide, tetrabutylammonium iodide, tetrabutylammonium hydrogensulfate, tetrabutylammonium hydroxide, tetrabutylammonium perchlorate, tetrabutylammonium tetrafluoroborate, tetrapropylammonium chloride, tetrapropylammonium bromide, tetrapropylammonium hydroxide, tetrahexylammonium bromide, tetrahexylammonium iodide, tetraoctylammonium bromide, cetyltrimethylammonium bromide, dodecyltrimethylammonium bromide, dodecyltrimethylammonium chloride, $C_{12}$-$C_{14}$-alkyltrimethylammonium borate, $C_{12}$-$C_{14}$-alkyltrimethylammonium diborate; N-phenyl($C_1$-$C_{18}$)trialkylammonium fluorides, chlorides or bromides, such as phenyltrimethylammonium chloride; N-benzyl($C_1$-$C_{18}$)trialkylammonium fluorides, chlorides or bromides, such as benzyltrimethylammonium chloride, benzyltriethylammonium chloride, benzyltriethylammonium bromide, benzyltributylammonium bromide;

pyridinium fluorides, chlorides or bromides, such as 1-cetylpyridinium chloride monohydrate, cetylpyridinium bromide.

Suitable phosphonium salts are, for example, tetraphenylphosphonium chloride or bromide, benzyltriphenylphosphonium chloride, benzyltriphenylphosphonium bromide; alkylphenylphosphonium chlorides, bromides, iodides, acetates, such as methyltriphenylphosphonium bromide, ethyltriphenylphosphonium bromide, ethyltriphenylphosphonium iodide, ethyltriphenylphosphonium acetate, butyltriphenylphosphonium chloride, butyltriphenylphosphonium bromide; tetraalkyl($C_1$-$C_{18}$)phosphonium chloride or bromide, such as tetrabutylphosphonium bromide.

Suitable polyglycols and crown ethers are, for example, diethylene glycol dibutyl ether ("butyl diglyme"), 18-crown-6 and dibenzo-18-crown-6.

Preference is given to using tetra($C_1$-$C_{18}$)alkylammonium hydrogensulfates and tetra($C_1$-$C_{18}$)alkylammonium chlorides, very preferably tetra($C_1$-$C_6$)alkylammonium hydrogensulfates and tetra($C_1$-$C_6$)alkylammonium chlorides.

Very particular preference is given to using tetra($C_1$-$C_{18}$) alkylammonium chlorides, extraordinary preference to using tetra($C_1$-$C_6$)alkylammonium chlorides.

Preference is likewise given to tetrabutylammonium fluoride, tetrabutylammonium hydrogensulfate, methyltributylammonium chloride, tetrapropylammonium chloride, tetrapropylammonium bromide, benzyltriphenylphosphonium chloride, benzyltriphenylphosphonium bromide or dibenzo-18-crown-6.

In general, the phase transfer catalyst is used in an amount of up to 20 mol %, preferably between 0.5 and 5 mol % and in particular between 0.3 and 2 mol %, based on the m-nitrobenzoyl chlorides II, preferably the fluorinated m-nitrobenzoyl chlorides IIA.

Very particular preference is given to using 0.01-20 mol %, more preferably 0.05-5 mol %, most preferably 0.1-2 mol % of the phase transfer catalyst based on the m-nitrobenzoyl chlorides II, preferably the fluorinated m-nitrobenzoyl chlorides IIA.

The multiphase system comprises an aqueous phase and at least one organic liquid phase. In addition, solid phases may also occur in the course of the reaction.

The aqueous phase is preferably a solution of alkali metal or alkaline earth metal hydroxides or carbonates in water. With regard to suitable alkali metal or alkaline earth metal hydroxides or carbonates, reference is made to the above statements. Particular preference is given to using alkali metal or alkaline earth metal hydroxides, especially sodium hydroxide or potassium hydroxide.

Useful substances for the organic phase are preferably aliphatic, cycloaliphatic or aromatic, optionally halogenated hydrocarbons, cyclic or open-chain ethers or mixtures thereof, reference being made to the above statements with regard to the aliphatic, cycloaliphatic or aromatic, optionally halogenated hydrocarbons, cyclic or open-chain ethers.

If the organic phase used is a water-miscible solvent, the reaction can also be carried out without a phase transfer catalyst.

In a preferred embodiment of the process according to the invention, the multiphase system consists of aqueous sodium hydroxide or potassium hydroxide solution as the aqueous phase and of toluene, chlorobenzene, dioxane, dichloroethane, dichloromethane, tetrahydrofuran or methyltetrahydrofuran, or of mixtures of these organic solvents as the organic phase.

In one particularly preferred embodiment of the process according to the invention the multiphase system is composed of aqueous sodium or potassium hydroxide solution as the aqueous phase and of unhalogenated or halogenated aromatic hydrocarbons such as toluene, xylene or chlorobenzene, for example, extraordinarily preferably of halogenated aromatic hydrocarbons such as chlorobenzene, for example, or of mixtures of these organic solvents, as the organic phase.

When a multiphase system is used, it is possible, for example, to initially charge m-nitrobenzoyl chloride II, preferably the fluorinated m-nitrobenzoyl chloride IIA, and the phase transfer catalyst without additional solvent or in one of the aforementioned organic solvents or solvent mixtures.

Thereafter, the aqueous solution of the base amount B2 and the reaction mixture resulting from step a) are added either successively or simultaneously with mixing and then the reaction is brought to completion within the desired temperature range.

When a multiphase system is used in step a) of the process according to the invention, the amino sulfone III is preferably introduced in an inert solvent. Subsequently B1 equivalents of base IV, i.e., 0.1-1.3 equivalents, preferably 0.1-1 equivalent, very preferably 0.2-0.7 equivalent, of base IV are added, advantageously offset over a certain period of time.

Subsequently, when using a multiphase system in step b), the phase transfer catalyst will preferably first be added to the reaction mixture resulting from step a).

Subsequently the m-nitrobenzoyl chloride II and also the amount of base B2 will be added. It is particularly preferred to add the m-nitrobenzoyl chloride II and also the amount of base B2 in parallel, very preferably in parallel and offset over a certain period of time, to the reaction mixture resulting from step a).

Alternatively, when using a multiphase system in step b) of the process according to the invention, it is possible first to add the m-nitrobenzoyl chloride II and also the amount of base B2 to the reaction mixture resulting from step a), and then to add the phase transfer catalyst.

The reaction can be carried out at standard pressure, reduced pressure or under elevated pressure, if appropriate under inert gas, continuously or batchwise.

The end of the reaction can easily be determined by the skilled worker by means of routine methods.

The reaction mixture can be worked up by the methods customary for the purpose. In general the solvent used is removed by customary methods, distillatively for example. The crude product can then be taken up in a non-water-miscible organic solvent, any impurities extracted with unacidified or acidified water, and the system can then be dried and the solvent removed under reduced pressure. For further purification it is possible to employ the typical methods such as crystallization, precipitation (for example by addition of an apolar solvent such as pentane, cyclohexane, heptane or toluene, or mixtures of said solvents) or chromatography.

When using a two-phase system it is usual to carry out extractive workup.

The end product can also be recovered by precipitation (e.g. by addition of an apolar solvent such as pentane, cyclohexane, heptane or toluene, or mixtures of the stated solvents).

In one preferred variant of the reaction in the process according to the invention, after the ending of the reaction, in a step c) the reaction mixture is diluted by addition of water and/or aqueous mineral acids, the pH of the aqueous phase being adjusted to pH≦7.

With particular preference the pH of the aqueous phase is adjusted to pH=2-6.5, with more particular preference to pH=3-5.0.

Aqueous mineral acids suitable for this purpose are aqueous mineral acids known to the skilled worker, such as hydrochloric acid, sulfuric acid, nitric acid or phosphoric acid, for example.

The reaction mixture can then be worked up by the methods customary therefor. In general, the phases are separated and the solvent used will be removed by customary processes, for example by distillation. For further purification, the customary processes such as for example crystallization (for example also by addition of a nonpolar solvent such as pentane, cyclohexane, heptane or toluene, or mixtures of the solvents mentioned) can be employed.

When a biphasic system is used, workup will generally be effected by extraction.

In a further preferred variant of the reaction in the process according to the invention, the dilute reaction mixture resulting from step c) is heated in a step d) and the phase separation is carried out at this temperature. This version of the process according to the invention is preferred primarily in those cases where step c) does not produce a clear solution.

Preferably the dilute reaction mixture obtained in step c) is heated to a temperature a short way beneath the boiling point and the phase separation is carried out at that temperature. Subsequently the product of value can be recovered by typical methods, such as removal of the solvent and, if appropriate, subsequent crystallization, for example.

Furthermore, the organic phase resulting from step d) can be subjected if necessary again to a step c) and, if appropriate, step d), it being possible for the repetition of steps c) and d) to take place as often as desired, preferably once.

The amino sulfones III required for the preparation of the sulfonamides I are known in the literature (Houben-Weyl, Methoden der organischen Chemie [Methods of organic chemistry] Vol. E11, 1985, p. 1019; Hamprecht et al., Angew. Chem. 93, 151, 1981) or can be prepared in accordance with the literature cited.

The m-nitrobenzoyl chlorides II required for the preparation of the sulfonamides I are known from the literature and can be prepared, for example, by reacting m-nitrobenzoic acids VII

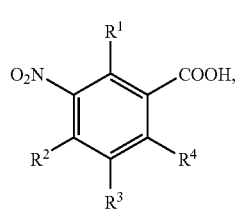

where the variables are each defined as follows:
R$^1$, R$^2$, R$^3$, R$^4$ are each hydrogen, halogen, cyano, nitro, C$_1$-C$_6$-alkyl, C$_1$-C$_6$-haloalkyl, C$_1$-C$_6$-alkoxy or C$_1$-C$_6$-haloalkoxy;
with chlorinating agents VIII.

The present invention accordingly further provides a process for preparing sulfonamides I wherein the m-nitrobenzoyl chlorides II required for the purpose are prepared from m-nitrobenzoic acids VII and chlorinating agents VIII.

In particularly preferred embodiments of the process according to the invention the variables R$^1$, R$^2$, R$^3$ and R$^4$ of the m-nitrobenzoyl chlorides II have the definitions stated above in connection with the sulfonamides I, more particularly the definitions stated there as being preferred, and, both considered alone and considered in combination with one another, they represent particular embodiments of the process according to the invention.

The preferred embodiments of the reaction of m-nitrobenzoic acids VII with chlorinating agents VIII are subject to the conditions stated below in connection with the reaction of fluorinated m-nitrobenzoic acids VIIA with chlorinating agents VIII in the presence of catalytic amounts of a phosphine derivative IX, more particularly the embodiments specified there as being preferred.

The prior art (for example WO 89/02891, WO 04/106324, WO 04/035545 and U.S. Pat. No. 6,251,829) describes in particular processes for preparing fluorinated benzoyl chlorides from fluorinated benzoic acids. However, the problem of eliminating the fluorine substituent occurs in the processes described in the prior art, in particular when catalysts such as N,N-dimethylaminopyridine (DMAP) or nitrogen bases such as pyridine, picoline or lutidine are used.

The fluoride released in turn has a damaging effect on the apparatus technology ("fluoride corrosion") and therefore entails correspondingly costly apparatus made of higher-value materials. Moreover, the elimination of the fluoride leads to contaminations or secondary components in the product of value.

However, when the process is carried out without catalyst, the yields are distinctly lower or higher reaction temperatures are required.

It is thus a further object of the present invention to provide a simple, economically viable and implementable process for preparing fluorinated m-nitrobenzoyl chlorides IIA, which firstly distinctly reduces fluoride elimination and simultaneously can achieve high yields and high purity of product of value.

We have found that, surprisingly, this object is achieved by a process in which fluorinated m-nitrobenzoic acids VII are reacted with chlorinating agents VIII, which comprises effecting the reaction in the presence of catalytic amounts of a phosphine derivative 1× and, if appropriate, in the presence of a Lewis acid.

Accordingly, the present invention further relates to a process for preparing fluorinated m-nitrobenzoyl chlorides IIA

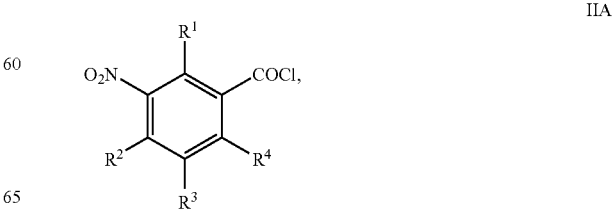

where the variables are each defined as follows:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
where at least one of the $R^1$ to $R^4$ radicals is fluorine,
by reacting fluorinated m-nitrobenzoic acids VIIA

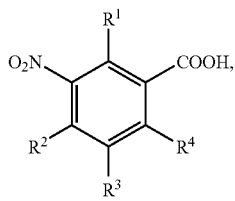

where the variables are each defined as follows:
$R^1$, $R^2$, $R^3$, $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
where at least one of the $R^1$ to $R^4$ radicals is fluorine,
with chlorinating agents VIII,
which comprises effecting the reaction in the presence of catalytic amounts of a phosphine derivative IX

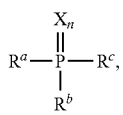

where the variables are each defined as follows:
$R^a$, $R^b$, $R^c$ are each $C_1$-$C_6$-alkyl or phenyl, which may optionally be substituted by $C_1$-$C_4$-alkyl;
X is oxygen or two single-bonded chlorine atoms;
n is 0 or 1.

The invention further relates to a process for preparing fluorinated sulfonamides IA (i.e. sulfonamides I where at least one of the radicals $R^1$ to $R^4$ is fluorine) wherein the fluorinated m-nitrobenzoyl chlorides IIA required for the purpose are prepared by the process stated above from fluorinated m-nitrobenzoic acids VII.

Specified below are the preferred embodiments of the reaction of fluorinated m-nitrobenzoic acids VIIA with chlorinating agents VIII in the presence of catalytic amounts of a phosphine derivative IX, with these embodiments, both considered alone and considered in combination with one another, representing special embodiments of the process according to the invention.

This process according to the invention for preparing fluorinated m-nitrobenzoyl chlorides IIA comprises the reaction of fluorinated m-nitrobenzoic acids VIIA with chlorinating agents VIII in the presence of catalytic amounts of a phosphine derivative IX:

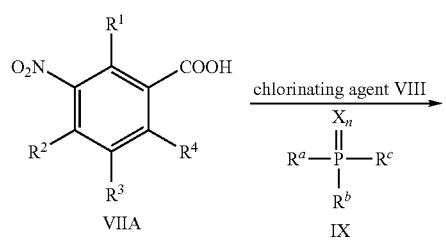

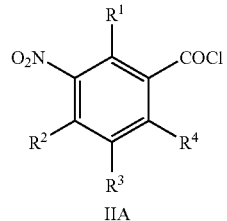

where the variables are each as defined above in conjunction with the preparation of fluorinated m-nitrobenzoyl chlorides IIA.

This reaction is effected typically at temperatures of from 20° C. to 160° C., preferably from 20° C. to 120° C., especially preferably from 70° C. to 120° C., in an inert organic solvent.

The reaction pressure during the process according to the invention may, for example, be in the range from 500 mbar to 10 bar. Preference is given to carrying out the reaction in the region of standard pressure, i.e. in the range from 0.9 to 1.2 bar.

The reaction time required for the reaction is generally in the range from 1 h to 24 h, in particular in the range from 2 h to 8 h.

The process according to the invention can in principle be carried out in substance. However, preference is given to carrying out the process according to the invention in an inert organic solvent.

In principle, all solvents which are capable of dissolving the fluorinated m-nitrobenzoic acids VIIA, the chlorinating agent and the phosphine derivative III at least partly and preferably fully under the reaction conditions are suitable.

Suitable solvents are, for example, aliphatic hydrocarbons such as pentane, hexane, cyclohexane and mixtures of $C_5$-$C_8$ alkanes, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisol and tetrahydrofuran, more preferably aromatic hydrocarbons or halogenated hydrocarbons.

It is also possible to use mixtures of the solvents mentioned.

The chlorinating agents VIII used are customary chlorinating agents such as oxalyl chloride, phosphorus trichloride, phosphorus pentachloride, thionyl chloride, phosphoryl chloride ($POCl_3$). It is also possible to use gaseous or liquid phosgene, corresponding dimers (trichloromethyl chloroformate, "diphosgene") or corresponding trimers bis(trichloromethyl) carbonate, "triphosgene") (cf. R. Beckert et al., Organikum, 22nd edition 2004, p. 496-499).

Preferred chlorinating agents VIII are oxalyl chloride, phosphorus trichloride, phosphorus pentachloride, thionyl chloride and phosphoryl chloride ($POCl_3$); thionyl chloride is very preferred.

The fluorinated m-nitrobenzoic acids VIIA and the chlorinating agent VIII are generally reacted with one another in equimolar amounts. It may be advantageous to use the chlorinating agent VIII in an excess based on the m-nitrobenzoic acids VIIA. Preference is given to using the chlorinating agent VIII and the fluorinated m-nitrobenzoic acids VIIA in a ratio of 2:1, more preferably 1.5:1.

The catalysts used are phosphine derivatives IX

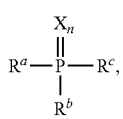

where the variables are each defined as follows:
$R^a$, $R^b$, $R^c$ are each $C_1$-$C_6$-alkyl or phenyl, which may optionally be substituted by $C_1$-$C_4$-alkyl;
X is oxygen or two single-bonded chlorine atoms;
n is 0 or 1.

Preference is given to using triphenylphosphine, triphenylphosphine oxide (TPPO), triphenyldichlorophosphine, tri($C_1$-$C_6$-alkyl)phosphine, tri($C_1$-$C_6$-alkyl)phosphine oxide and tri($C_1$-$C_6$-alkyl)dichlorophosphine;
more preferably triphenylphosphine, triphenylphosphine oxide and tri($C_1$-$C_6$-alkyl)phosphine oxide;
exceptionally preferably triphenylphosphine oxide.

The phosphine derivative IX is used generally in amounts of from 0.01 to 5 mol %, preferably from 0.1 to 1 mol %, more preferably from 0.1 to 0.5 mol %, based on the amount of fluorinated m-nitrobenzoic acid VII used.

Moreover, the process according to the invention may additionally be carried out in the presence of Lewis acids. The Lewis acids used are customary Lewis acids (cf., for example, Lewis Acids in Organic Synthesis, ed. H. Yamamoto, Vol. 1 and 2, Weinheim 2000).

Suitable Lewis acids are in particular boron compounds such as
boron halides (e.g. $BF_3$, $BCl_3$, $BF_3$ etherate), boric acid ($H_3BO_3$), boric anhydride, boric esters (e.g. tri-$C_1$-$C_4$-alkyl borate), borate (e.g. sodium borate/borax),
boronic acids (e.g. $C_1$-$C_6$-alkylboronic acids, arylboronic acids, especially phenylboronic acid), $C_1$-$C_4$-alkyl boronates (e.g. $C_1$-$C_6$-alkyl $C_1$-$C_4$-alkyl boronates, $C_1$-$C_4$-alkyl aryl boronates), cyclic boric esters (e.g. tris($C_1$-$C_4$-alkoxy) boroxin, especially trimethoxyboroxin, and triethanolamine borate).

Particular preference is given to boric acid, tri-$C_1$-$C_4$-alkyl borates or cyclic boric esters.

The Lewis acid is used generally in amounts of from 0.01 to 5 mol %, preferably from 0.1 to 1 mol %, based on the amount of m-nitrobenzoic acid II used.

The process can be carried out either continuously or discontinuously (batchwise or semibatchwise).

In the process according to the invention, the reactants and reagents can in principle be combined in any sequence, i.e. the reactants and the phosphine derivative IX and, if appropriate, the Lewis acid may be introduced separately, simultaneously or successively into the reaction vessel and reacted.

Advantageously, the fluorinated m-nitrobenzoic acid VIIA and the phosphine derivative IX and, if appropriate, the Lewis acid are initially charged in an inert solvent and the chlorinating agent VIII is added with mixing, for example stirring. However, it is also possible to initially charge the chlorinating agent VIII together with the phosphine derivative IX and, if appropriate, the Lewis acid, and then to add the fluorinated m-nitrobenzoic acid VIIA, preferably dissolved in an inert solvent.

The reaction mixtures may be worked up in a customary manner, for example by distilling off the solvent and removing the excess chlorinating reagent. Some of the end products are obtained in the form of viscous oils which can be freed of volatile fractions or purified under reduced pressure and at moderately elevated temperature. When the intermediates and end products are obtained as solids, the purification can also be effected by recrystallization or digestion.

Preference is given to not effecting any further purification after the reaction has ended.

The fluorinated m-nitrobenzoic acids IIA required for the preparation of the fluorinated m-nitrobenzoyl chlorides VIIA are known in the literature or can be prepared by nitrating the corresponding benzoic acids or by nitrating the corresponding methyl benzoates and subsequently hydrolyzing (for example, R. Beckert et al., Organikum, 22nd edition 2004, p. 358-361).

The fluorinated m-nitrobenzoyl chlorides IIA obtainable by the process according to the invention may be used as starting materials for the preparation of sulfonamides IA which are themselves valuable intermediates for the synthesis of pharmacologically active compounds or crop protection compositions.

The present invention therefore further provides a process for preparing sulfonamides IA starting from fluorinated m-nitrobenzoyl chlorides IA.

Depending on the substitution pattern, the fluorinated m-nitrobenzoyl chlorides HA may comprise one or more centers of chirality and are then present in the form of an enantiomeric or diastereomeric mixtures. The invention thus provides a process for preparing either the pure enantiomers or diastereomers, or their mixtures.

The organic molecular moieties specified for the substituents $R^1$ to $R^6$ and $R^a$, $R^b$ and $R^c$ constitute, according to the meanings indicated above, collective terms for individual lists of the individual group members. All hydrocarbon chains, i.e. all alkyl, haloalkyl, alkoxy and haloalkoxy moieties, may be straight-chain or branched.

Unless stated otherwise, halogenated substituents preferably bear from one to five identical or different halogen atoms. The term halogen in each case represents fluorine, chlorine, bromine or iodine.

In conjunction with the fluorinated m-nitrobenzoyl chlorides IIA, the variables $R^1$, $R^2$, $R^3$ and $R^4$ are each as defined above, in particular the meanings indicated as being preferred, where at least one of the $R^1$ to $R^4$ radicals in the combination of all four $R^1$ to $R^4$ radicals is fluorine, these abovementioned definitions, alone and also in combination with one another, constituting particular embodiments of the process according to the invention.

Preference is given to the embodiment of the process according to the invention in which
$R^1$ is hydrogen, halogen or $C_1$-$C_6$-alkyl;
preferably hydrogen or halogen;
very preferably hydrogen, fluorine or chlorine;
more preferably hydrogen.

Equally preferred is the embodiment of the process according to the invention in which
$R^2$ is hydrogen, halogen, cyano, $C_1$-$C_6$-alkyl or $C_1$-$C_6$-haloalkyl;
preferably hydrogen or halogen;
very preferably hydrogen, fluorine or chlorine;
more preferably hydrogen or fluorine;
exceptionally preferably hydrogen;
equally exceptionally preferably fluorine.

Also preferred is the embodiment of the process according to the invention in which
$R^2$ is hydrogen or halogen;
preferably halogen;
very preferably fluorine or chlorine;
more preferably fluorine.

Equally preferred is the embodiment of the process according to the invention in which $R^3$ is hydrogen, halogen or $C_1$-$C_6$-alkyl;
preferably hydrogen or halogen;
very preferably hydrogen, fluorine or chlorine;
more preferably hydrogen.

Equally preferred is the embodiment of the process according to the invention in which $R^4$ is hydrogen, halogen, cyano, $C_1$-$C_6$-alkyl or $C_1$-$C_6$-haloalkyl;
preferably hydrogen, halogen or cyano;
very preferably hydrogen, fluorine, chlorine or cyano;
more preferably hydrogen, chlorine or cyano;
exceptionally preferably hydrogen;
equally exceptionally preferably chlorine or cyano;
very exceptionally preferably chlorine.

Also preferred is the embodiment of the process according to the invention in which $R^4$ is halogen or cyano;
preferably halogen;
very preferably fluorine or chlorine;
more preferably chlorine.

Also preferred is the embodiment of the process according to the invention in which $R^4$ is hydrogen, halogen or cyano;
preferably hydrogen or halogen;
very preferably hydrogen, fluorine or chlorine;
more preferably hydrogen or chlorine.

In a very preferred embodiment of the process according to the invention, the variables $R^1$, $R^2$, $R^3$ and $R^4$ are each defined as follows:

$R^1$ is hydrogen;
$R^2$ is hydrogen or halogen;
preferably halogen;
very preferably fluorine;
$R^3$ is hydrogen; and
$R^4$ is hydrogen, chlorine or cyano;
preferably chlorine or cyano;
very preferably chlorine.

In a further very preferred embodiment of the process according to the invention, the variables $R^1$, $R^2$, $R^3$ and $R^4$ are each defined as follows:

$R^1$ is hydrogen;
$R^2$ is hydrogen or halogen;
preferably halogen;
very preferably fluorine;
$R^3$ is hydrogen; and
$R^4$ is hydrogen or halogen;
preferably hydrogen or chlorine;
very preferably chlorine;
equally very preferably hydrogen.

In a further very preferred embodiment of the process according to the invention, the variables $R^1$, $R^2$, $R^3$ and $R^4$ are each defined as follows:

$R^1$ is hydrogen;
$R^2$ is fluorine;
$R^3$ is hydrogen; and
$R^4$ is halogen;
preferably chlorine.

In an exceptionally preferred embodiment of the process according to the invention, fluorinated m-nitrobenzoyl chlorides IIA.a (corresponds to formula IIA where $R^1$=fluorine)

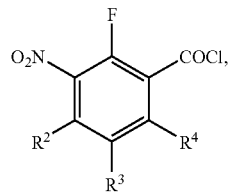

can be prepared, where $R^2$, $R^3$ and $R^4$ are each as defined above, especially as defined above with preference.

In a further exceptionally preferred embodiment of the process according to the invention, fluorinated m-nitrobenzoyl chlorides IIA.b (corresponds to formula IIA where $R^2$=fluorine)

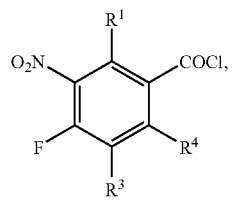

can be prepared, where $R^1$, $R^3$ and $R^4$ are each as defined above, especially as defined above with preference.

In a further exceptionally preferred embodiment of the process according to the invention, fluorinated m-nitrobenzoyl chlorides IIA.c (corresponds to formula IIA where $R^3$=fluorine)

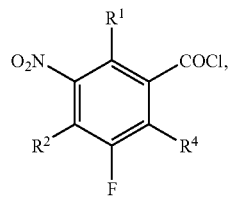

can be prepared, where $R^1$, $R^2$ and $R^4$ are each as defined above, especially as defined above with preference.

In a further exceptionally preferred embodiment of the process according to the invention, fluorinated m-nitrobenzoyl chlorides IIA.d (corresponds to formula IIA where $R^4$=fluorine)

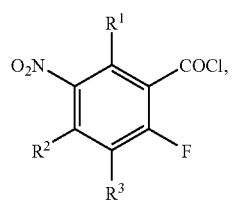

can be prepared, where $R^1$, $R^2$ and $R^3$ are each as defined above, especially as defined above with preference.

In a further exceptionally preferred embodiment of the process according to the invention, fluorinated m-nitrobenzoyl chlorides IIA.e (corresponds to formula IA where $R^1$ and $R^3$=H)

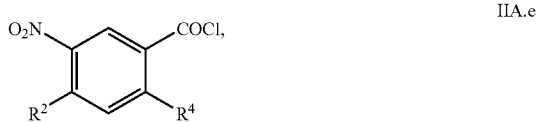

IIA.e can be prepared, where the variables $R^2$ and $R^4$ are each as defined above, especially as defined above with preference, and where at least one of the $R^2$ and $R^4$ radicals is fluorine.

In addition it is also possible to prepare m-nitrobenzoyl chlorides II by hydrolyzing the corresponding benzotrichlorides X in the presence of a catalyst or in a weakly acidic medium.

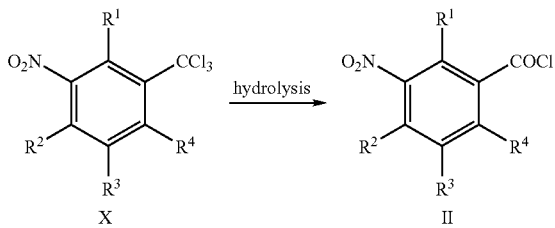

where the variables are each defined as follows:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy.

The present invention accordingly relates additionally to a process for preparing sulfonamides I wherein the m-nitrobenzoyl chlorides II required for the purpose are prepared by hydrolyzing benzotrichlorides X in the presence of a catalyst or in a weakly acidic medium.

In particularly preferred embodiments of the process according to the invention the variables $R^1$, $R^2$, $R^3$ and $R^4$ of the m-nitrobenzoyl chlorides II have the definitions specified above in connection with the sulfonamides I, more particularly the definitions specified there as being preferred, which, considered both alone and in combination with one another, represent special embodiments of the process according to the invention.

The preferred embodiments of the hydrolysis of corresponding benzotrichlorides X are subject to the conditions specified below in connection with the hydrolysis of fluorinated m-nitrobenzotrichlorides XA, more particularly the embodiments specified there as being preferred.

In the prior art (e.g. O, Scherer et al., Liebigs Ann. Chem. 1964, 677, 83-95; WO 06/090210) processes are described for preparing aromatic acid chlorides from the corresponding benzoic acids. Under the reaction conditions described in the prior art, however, the problem occurs of the elimination of fluorine substituents located on the aromatic structure.

The fluoride released has the disadvantages such as those already outlined above in connection with the preparation of benzoyl chlorides from the corresponding benzoic acids.

Accordingly a further object of the present invention is to provide a process for preparing fluorinated m-nitrobenzoyl chlorides IIA by hydrolysis of corresponding fluorinated m-nitrobenzotrichlorides XA which significantly reduces the elimination of fluoride, it being possible at the same time to obtain high yields and a high purity of the product of value.

It has surprisingly been found that this object is achieved by means of a process wherein fluorinated m-nitrobenzotrichlorides XA are hydrolyzed in the presence of a catalyst or in a weakly acidic medium at temperatures less than 80° C.

The present invention accordingly further provides a process for preparing fluorinated m-nitrobenzoyl chlorides IIA

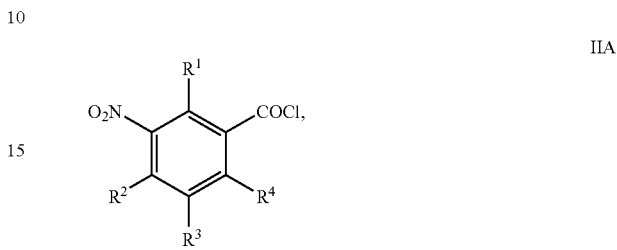

IIA where the variables are each defined as follows:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
where at least one of the radicals $R^1$ to $R^4$ is fluorine,
by hydrolyzing fluorinated m-nitrobenzotrichlorides XA

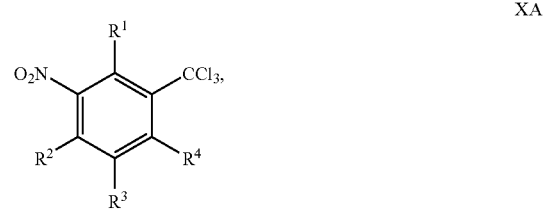

XA where the variables $R^1$, $R^2$, $R^3$ and $R^4$ are each as defined above,
wherein the reaction takes places in the presence of a catalyst or in a weakly acidic medium and also at temperatures less than 80° C.

The present invention further provides a process for preparing fluorinated sulfonamides IA, wherein the fluorinated m-nitrobenzoyl chlorides IIA required for the purpose are prepared by the above-specified process from fluorinated m-nitrobenzotrichlorides XA.

The variables $R^1$, $R^2$, $R^3$ and $R^4$ have the definitions stated beforehand in connection with the fluorinated m-nitrobenzoyl chlorides IIA, more particularly the definitions stated beforehand as being preferred, at least one of the radicals $R^1$ to $R^4$ in the combination of all four radicals $R^1$ to $R^4$ being fluorine, and where these aforementioned definitions, considered both alone and in combination with one another, represent special embodiments of the process according to the invention.

The preferred embodiments of the hydrolysis of the fluorinated m-nitrobenzo-trichlorides XA to fluorinated m-nitrobenzoyl chlorides IIA are outlined below, and, considered both alone and in combination with one another, represent special embodiments of the process according to the invention.

The hydrolysis of fluorinated m-nitrobenzotrichlorides XA to fluorinated m-nitrobenzoyl chlorides IIA takes place at temperatures less than 80° C. (<80° C.), preferably between 29 and <80° C., very preferably between 49° C. and <80° C., with particular preference between 59° C. and <80° C., if appropriate in an inert organic solvent in the presence of an acid and/or a catalyst.

Suitable solvents are aliphatic hydrocarbons such as pentane, hexane, cyclohexane and mixtures of $C_5$-$C_8$ alkanes, halogenated hydrocarbons such as methylene chloride and chloroform, ethers such as diethyl ether, diisopropyl ether, tert-butyl methyl ether, dioxane and tetrahydrofuran, ketones such as tert-butyl methyl ketone, and also dimethylformamide and dimethylacetamide, particular preference being given to aliphatic hydrocarbons and halogenated hydrocarbons.

Mixtures of the stated solvents can also be used.

The reaction of the fluorinated m-nitrobenzotrichlorides XA to fluorinated m-nitrobenzotrichlorides IIA can also be carried out solvent-free in the melt at temperatures <80° C., preferably from 60 to <80° C., more preferably from 60 to 75° C. This version of the reaction regime is preferred.

It is preferred to add 1 equivalent of water to the reaction mixture, based on the fluorinated m-nitrobenzotrichloride XA. Advantageously the water is added uniformly over a certain period of time, e.g. over the course of 1 to 12 h, preferably over the course of 2 to 6 h.

Acids used are inorganic acids such as hydrochloric acid, hydrobromic acid and sulfuric acid, and also organic acids such as formic acid, acetic acid, propionic acid, oxalic acid, toluenesulfonic acid, benzenesulfonic acid, camphor sulfonic acid, citric acid and trifluoroacetic acid, with particular preference sulfuric acid, e.g. aqueous sulfuric acid, or oleum.

The acids are used generally in an equimolar amount, but may also be used catalytically.

Suitable catalysts are Lewis acids such as iron(III) chloride, iron sulfate, cerium(III) chloride or copper(II) chloride; iron(III) chloride is particularly preferred. It is preferred to use 0.003-0.1 equivalent, more preferably 0.003-0.001, very preferably 0.003-0.006 equivalent of the catalyst in relation to the benzotrichloride X.

The reaction of the fluorinated m-nitrobenzotrichlorides XA to fluorinated m-nitrobenzotrichlorides IIA can also be carried out only in the presence of a suitable catalyst, without additional acid. This version of the reaction regime is preferred.

The reaction mixtures are worked up by customary methods known to the skilled worker, such as by removing the solvent, for example. The catalyst can be removed by extraction methods known to the skilled worker, as for example by dissolving the reaction mixture in a suitable solvent, such as in aromatic hydrocarbons such as toluene, o-, m- and p-xylene and chlorobenzene, preferably chlorobenzene, and then carrying out extraction with aqueous mineral acids such as hydrochloric acid or sulfuric acid.

Alternatively the reaction mixture obtained can also be supplied in the form of its melt directly to the next reaction stage, without further purification.

The fluorinated m-nitrobenzotrichlorides XA required for preparing the fluorinated m-nitrobenzoyl chlorides IIA are known in the literature [e.g. WO 06/090210] or can be prepared in accordance with the cited literature.

Furthermore, m-nitrobenzoyl chlorides II can also be prepared by the reaction of corresponding benzotrichlorides X with m-nitrobenzoic acids VII in the presence of a catalyst:

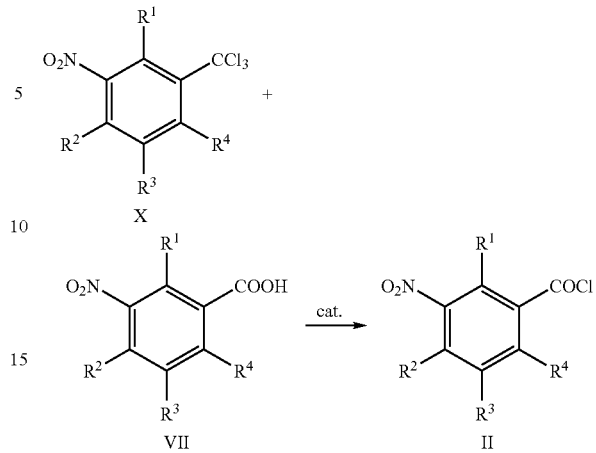

More particularly it is also possible to prepare fluorinated m-nitrobenzoyl chlorides IIA by the reaction of fluorinated m-nitrobenzotrichlorides XA with fluorinated m-nitrobenzoic acids VIIA in the presence of a catalyst:

The variables $R^1$, $R^2$, $R^3$ and $R^4$ have the definitions stated above in connection with the m-nitrobenzoyl chlorides II, and/or the fluorinated m-nitrobenzoyl chlorides IIA, more particularly the definitions stated above as being preferred, and these aforementioned definitions, both considered alone and considered in combination with one another, represent special embodiments of the process according to the invention.

The present invention accordingly further provides a process for preparing sulfonamides I, more particularly fluorinated sulfonamides IA, wherein the m-nitrobenzoyl chlorides II required for the purpose, more particularly the fluorinated m-nitrobenzoyl chlorides IIA, are prepared by the aforementioned process from benzotrichlorides X and m-nitrobenzoic acids VII, more particularly from benzotrichlorides XA and fluorinated m-nitrobenzoic acids VIIA.

Described below are the preferred embodiments of the reaction of the benzotrichlorides X and m-nitrobenzoic acids VII to form m-nitrobenzoyl chlorides II, and these embodiments, considered both alone and in combination with one another, represent special embodiments of the process according to the invention.

This reaction of the benzotrichlorides X with m-nitrobenzoic acids VII takes place typically at temperatures of 70° C. to 160° C., preferably 70° C. to 120° C., with particular preference 80° C. to 110° C., if appropriate in an inert organic solvent in the presence of a catalyst.

Suitable solvents are aliphatic hydrocarbons such as pentane, hexane, cyclohexane and mixtures of $C_5$-$C_8$ alkanes, halogenated hydrocarbons such as methylene chloride and chloroform, ethers such as diethyl ether, diisopropyl ether, tert-butyl methyl ether, dioxane and tetrahydrofuran, ketones such as tert-butyl methyl ketone, and also dimethylformamide and dimethylacetamide; particular preference is given to aliphatic hydrocarbons and halogenated hydrocarbons.

Mixtures of the stated solvents can be used as well.

The reaction of the benzotrichlorides X with m-nitrobenzoic acids VII to m-nitrobenzotrichlorides II can also be carried out solventlessly in the melt at temperatures of 70 to 120° C., preferably 80 to 110° C. This version of the reaction regime is preferred.

Suitable catalysts are Lewis acids such as iron(III) chloride, iron sulfate, cerium(III) chloride or copper(II) chloride, for example, particular preference being given to iron(III) chloride.

It is preferred to use 0.003-0.1 equivalent, with particular preference 0.003-0.001 equivalent, very preferably 0.003-0.006 equivalent of the catalyst in relation to the benzotrichloride X.

The benzotrichlorides X and m-nitrobenzoic acids VII are preferably reacted with one another in equimolar amounts.

The reaction mixtures are worked up by customary methods known to the skilled worker, such as by removing the solvent, for example. The catalyst can be removed by extraction methods known to the skilled worker, as for example by dissolving the reaction mixture in a suitable solvent, such as in aromatic hydrocarbons such as toluene, o-, m- and p-xylene and chlorobenzene, preferably chlorobenzene, and then carrying out extraction with aqueous mineral acids such as hydrochloric acid or sulfuric acid.

Alternatively the reaction mixture obtained can be supplied in the form of its melt directly to the next reaction stage, without further purification.

The sulfonamides I and IA obtainable in accordance with the processes according to the invention can be used as starting materials for the preparation of aniline derivatives VI, which in turn are valuable intermediates for the synthesis of pharmacologically active compounds or crop protection agents.

A further subject matter of the present invention, therefore, is the provision of a process for preparing aniline derivatives VI by reducing sulfonamides I prepared beforehand by the abovementioned processes according to the invention:

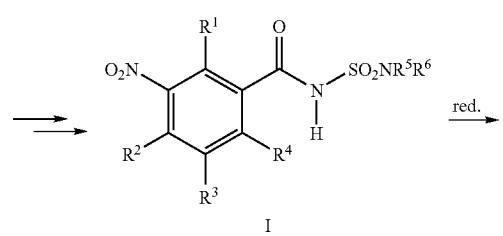

I

-continued

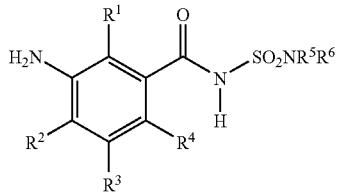

VI

In connection with the aniline derivatives VI the variables $R^1$, $R^2$, $R^3$, $R^4$, $R^5$ and $R^6$ have the definitions stated above in connection with the sulfonamides I, more particularly the definitions stated above as being preferred, and these aforementioned definitions, considered both alone and in combination with one another, represent special embodiments of the process according to the invention.

The reduction of the sulfonamides I to aniline derivatives VI is accomplished, for example, using nascent hydrogen. For this purpose the nitro compound is reacted with an acid in the presence of a base metal. Base metals are of course those which are dissolved by a Brönsted acid with evolution of hydrogen. Metals of this kind generally have a standard potential <0 V and more particularly less than or equal to −0.1 V, e.g. in the range from −0.1 to −1.0 V (in acidic aqueous solution at 15° C. and 1 bar). Examples of suitable metals are Zn, Fe and Sn, more particularly Fe. Acids contemplated for this purpose include not only inorganic mineral acids, examples being hydrochloric acid or dilute sulfuric acid, or mixtures of inorganic acid and one of the aforementioned solvents, gaseous HCl in an ether or an alcohol or a mixture thereof, for example, or organic carboxylic acids, appropriately acetic acid, propionic acid or butyric acid.

The reaction conditions correspond substantially to the reaction conditions employed for the reduction of aliphatic or aromatic nitro groups to aliphatic or aromatic amino groups using nascent hydrogen (see, for example, H. Koopman, Rec. Trav. 80 (1961), 1075).

Depending on the nature of the metal and acid, the reaction temperature is situated generally in the range from −20 to +120° C., preference being given, when using alkanoic acids such as acetic acid, to using temperatures in the range from 50 to 100° C. The reaction time can be from a few minutes to several hours, e.g. about 20 minutes to 5 hours. Preferably the sulfonamide I for reduction is charged to the reaction vessel and then the respective metal, preferably in finely divided form, more particularly as a powder, is added to the reaction mixture with thorough mixing. The addition takes place preferably over a period of 10 minutes to 2 hours. It is of course also possible to introduce the metal and the acid initially and to add the sulfonamide I, if appropriate together with an inert solvent. Frequently the reaction mixture is left to afterreact at reaction temperature for a certain additional period, e.g. 10 minutes to 4 hours.

The reduction of I to VI is preferably conducted with iron powder in dilute acid. Suitable acids are mineral acids such as hydrochloric acid or organic acids such as formic acid, acetic acid, propionic acid, butyric acid. Preference is given to using acetic acid. The amount of iron powder is preferably 2 to 5 mol, more particularly 2.5 to 4 mol, per mole of the sulfonamide I. The amount of acid is generally not critical. Appropriately at least an equimolar amount of acid is used, based on the sulfonamide I, in order that reduction of the starting compound is as near complete as possible. The reaction can be carried out continuously or discontinuously. The reaction temperatures are in that case in the range from 50 to 100° C., preferably 65 to 75° C. In one embodiment, for example, the iron powder is introduced initially in acetic acid and then the sulfonamide I is introduced into the reaction vessel. The addition takes place preferably over the course of 20 to 60 minutes with the constituents being mixed, by stirring for example. After the end of the addition the reaction is allowed to continue for 0.5 to 2 hours more, preferably about 1 hour, at reaction temperature. Alternatively the iron powder can also be added with stirring to the mixture of the sulfonamide I in glacial acetic acid and the reaction can be completed as described above.

The working-up for obtaining aniline derivative VI can take place by the methods that are customary for that purpose. Generally speaking the solvent will first be removed, by distillation, for example. For further purification it is possible to employ customary techniques such as crystallization, chromatography, on silica gel for example, stirring with a solvent, examples being aromatic hydrocarbons such as benzene, toluene, xylene or aliphatic hydrocarbons such as petroleum ether, hexane, cyclohexane, pentane, carboxylic esters such as ethyl acetate, etc, and mixtures thereof.

Also suitable as reducing agents, furthermore, are metal hydrides and semimetal hydrides such as aluminum hydride and hydrides derived therefrom such as lithium aluminum hydride, diisobutylaluminum hydride, boron hydrides such as diborane, and boronates derived therefrom, such as sodium borohydride or lithium boronate. For this purpose the sulfonamide I is contacted with the complex metal hydride in an inert solvent at 10 to 65° C., advantageously 20 to 50° C. The reaction time is preferably 2 to 10 hours, and advantageously 3 to 6 hours. The reaction is preferably conducted in an organic solvent that is inert toward the reducing agent. Suitable solvents include—depending on the reducing agent selected—e.g. alcohols, examples being $C_1$-$C_4$ alcohols such as methanol, ethanol, n-propanol, isopropanol or n-butanol, and mixtures thereof with water, or ethers such as diisopropyl ether, methyl tert-butyl ether, ethylene glycol dimethyl ether, dioxane or tetrahydrofuran.

In general 0.5 to 3, advantageously 0.75 to 2.5, mol of metal hydride, metal hemihydride, boron hydride and/or boronate is used per mole of sulfonamide I. The process follows the procedure described in Organikum, VEB Deutscher Verlag der Wissenschaften, Berlin 1976, 15th edition, pp. 612-616.

A further suitable reducing agent for the conversion of the sulfonamide I into the aniline derivative VI is hydrogen in the presence of catalytic amounts of a transition metal catalyst, more particularly with transition metals from transition group 8. This reduction of the sulfonamides I to aniline derivatives VI with hydrogen is preferred.

Outlined below are the preferred embodiments of this reduction, which, considered both alone and in combination with one another, represent special embodiments of the process according to the invention.

The reaction takes place typically at temperatures of 0° C. to 100° C., preferably at 10° C. to 50° C., either solventlessly or in an inert solvent (cf. e.g. Tepko et al., J. Org. Chem. 1980, 45, 4992).

Depending on the solubility of the substrate for hydrogenation, suitable solvents are aliphatic hydrocarbons such as pentane, hexane, cyclohexane and mixtures of $C_5$-$C_8$ alkanes; aromatic hydrocarbons such as toluene, o-, m- and p-xylene; halogenated hydrocarbons such as methylene chloride, chloroform and chlorobenzene; ethers such as diethyl ether, diisopropyl ether, tert-butyl methyl ether, dioxane, anisole and tetrahydrofuran; carboxylic esters such as ethyl acetate; nitriles such as acetonitrile and propionitrile; ketones such as acetone, methyl ethyl ketone, diethyl ketone and tert-butyl methyl ketone; alcohols such as methanol, ethanol, n-propanol, isopropanol, n-butanol and tert-butanol; and also dimethyl sulfoxide, dimethylformamide and dimethylacetamide, carboxylic acids such as acetic acid, or aqueous solutions of organic acids such as acetic acid and water, with particular preference alcohols such as methanol, ethanol, n-propanol, isopropanol, n-butanol and tert-butanol; aromatic hydrocarbons such as toluene, o-, m- and p-xylene and also chlorobenzene.

It is also possible to use mixtures of the stated solvents. In addition it is also possible to operate without solvent.

Preferred transition metal catalysts comprise a transition metal from the group Ni, Pd, Pt, Ru, Rh and Ir. Particular preference is given to palladium, platinum, ruthenium and iridium.

The transition metal catalysts can be used as they are or in supported form. Preference is given to using supported catalysts. Examples of supports are activated carbon, alumina, $ZrO_2$, $TiO_2$, $SiO_2$, carbonates and the like, preferably activated carbon.

It is also possible to use transition metal catalysts doped with various transition group elements, e.g. copper, iron, nickel or vanadium, in various proportions.

The transition metals can also be used in the form of activated metals such as Raney nickel or in the form of compounds.

Furthermore, the transition metals can also be used in the form of compounds. Suitable transition metal compounds are, for example, palladium oxide and platinum oxide. Also suitable are noble metal sulfides such as platinum sulfide (cf. Houben-Weyl, Methoden der organischen Chemie, vol. IV/1C, pp. 520-526).

The catalysts are used generally in an amount of 0.005 to 10 mol % (calculated as metal), preferably 0.001 to 10 mol %, more preferably 0.0055 to 2 mol %, with particular preference 0.005 to 0.5 mol %, based in each case on the sulfonamide I for reduction.

The reduction can be carried out under standard hydrogen pressure or under elevated hydrogen pressure, with for example a hydrogen pressure of 0.01 to 50 bar, preferably 0.1 to 40 bar, with particular preference from 1 to 20 bar, with especial preference 1 to 16 bar.

If appropriate the nitro compounds of the formula II are purified prior to the hydrogenation by means of extractive stirring with activated carbon or recrystallization from an organic solvent by addition of a second solvent, e.g. acetone/water.

In the case of chlorinated sulfonamides I the hydrogenation is carried out—depending on the sensitivity of the substituent—preferably at 20 to 170° C., with particular preference at 20 to 140° C., with great preference at 20 to 80° C.

In the case of sulfonamides I having reactive halogen substituents it is further advisable to carry out hydrogenation in neutral solution, where appropriate with only slightly elevated pressure, with small amounts of nickel, palladium, platinum, ruthenium, rhodium or else iridium catalysts. Noble metal sulfides such as platinum sulfide are also suitable.

The reaction mixture is worked up after the catalyst has been separated off by known methods. Generally speaking, first the solvent is removed, by distillation for example. For further purification it is possible to employ typical techniques such as extraction, crystallization, chromatography (on silica gel, for example) or stirring with a solvent (aromatic hydrocarbons, for example, such as benzene, toluene or xylene, or aliphatic hydrocarbons, for example, such as petroleum ether, hexane, cyclohexane, pentane, carboxylic esters such as ethyl acetate, etc, and mixtures thereof).

The reduction of the sulfonamides I to aniline derivatives VI can also take place with sodium sulfide, advantageously in aqueous ammoniacal solution, in the presence of ammonium chloride. The reaction temperature is generally between 40 to 90° C., preferably between 60 to 80° C. It is judicious to use 3 to 4 mol of sodium sulfide per mole of sulfonamide I.

The examples which follow serve to further illustrate the invention:

1. PREPARATION OF THE FLUORINATED M-NITROBENZOYL CHLORIDES IIA

The Yields of Fluorinated m-Nitrobenzoyl Chloride IIA were, Unless Stated Otherwise, Determined by Means of Quantitative HPLC:

Sample Preparation:

First, the fluorinated m-nitrobenzoyl chlorides IIA formed as the product were converted to the corresponding methyl esters. To this end, the samples of the fluorinated m-nitrobenzoyl chlorides IIA to be determined were weighed into a 100 ml standard flask which was made up to 100 ml with methanol. The mixture was left to stir at room temperature for a further 10 min.

Chromatographic Conditions:

Column: symmetry C18 5 μm 250×4.6 mm from Waters®

Wavelength: 222 nm

Eluent: gradient of A (0.1% by volume of $H_3PO_4$ in $H_2O$) and B (0.1% by volume of $H_3PO_4$ in $CH_3CN$); 10 min 70% B, then B rising from 70% to 100% within 15 min, then back to 35% within 2 min, then 7 min 35% B.

Flow rate: 1 ml/min

Pressure: approx. 150 bar

Calibration:

The calibration was effected with external standard (corresponding methyl nitrobenzoate). To establish the standard, a total of 5 samples of the pure substances were weighed in the following concentrations (precision +/−0.1 mg): approx. 0.1 g/l, approx. 0.2 g/l, approx. 0.3 g/l, approx. 0.4 g/l, approx. 0.5 g/l.

With the aid of a suitable PC program, a calibration line was established. For the substances detailed above, this was a linear function. Standard deviation, correlation coefficient and straight-line equation were calculated.

For each of the components, their concentration can thus be determined based on the particular external standard.

The Fluoride Values were Determined by Means of the Following Test Method:

1-2 ml of the sample were extracted with 50 ml of demineralized water. After the aqueous phase had been removed, depending on the concentration expected, an aliquot part thereof was used for the measurement.

The measurement was effected in a buffer solution (TISAB) at pH 5.26 by means of an ion-selective electrode (measurement concentration >1 mg/l of fluoride; detection limit <25 mg/l of fluoride).

The error limit is +/−0.002 g/l.

The following units were used:

| | |
|---|---|
| Ion-sensitive fluoride electrode | e.g. Metrohm 6.0502.150 |
| Reference electrode | e.g. Metrohm 6.0733.100 |
| Ion meter | e.g. Radiometer PHM 250 |

Example 1.1

4-fluoro-5-nitrobenzoyl chloride (with TPPO)

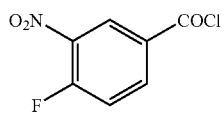

18.5 g (0.1 mol) of 4-fluoro-5-nitrobenzoic acid and 0.1 g (0.00036 mol) of triphenylphosphine oxide (TPPO) were initially charged in chlorobenzene and the suspension was heated at 95° C. with stirring. Subsequently, 16.8 g (0.14 mol) of thionyl chloride were added within 10 min. The reaction mixture was stirred at 105-110° C. for a further 2 h.

Subsequently, the reaction mixture was allowed to cool to room temperature and the fluoride content of the solution was determined, which was 0.01 g/l.

Subsequently, the solvent and excess thionyl chloride were removed by distillation. After addition of chlorobenzene, 40.8 g (98% of theory; determined by means of $^{19}$F-NMR with internal standard) of the title product were obtained as a solution in chlorobenzene.

The following examples 1.2 to 1.9 were carried out analogously to example 1.1.

Example 1.2

2-chloro-4-fluoro-5-nitrobenzoyl chloride (with TPPO)

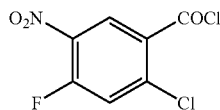

22.3 g (0.1 mol) of 2-chloro-4-fluoro-5-nitrobenzoic acid
16.8 g (0.14 mol) of thionyl chloride
0.1 g (0.00036 mol) of triphenyl phosphine oxide
Yield*: 46.5 g (>99% of theory) of the title compound as a solution in chlorobenzene

* In these examples, the yield was determined by means of $^{19}$F-NMR with internal standard.

Fluoride value: 0.01 g/l

Example 1.3

4-fluoro-5-nitrobenzoyl chloride (without catalyst)

18.5 g (0.1 mol) of 4-fluoro-5-nitrobenzoic acid
16.8 g (0.14 mol) of thionyl chloride
Yield*: 47.3 g (86% of theory) of the title compound as a solution in chlorobenzene
Fluoride value: 0.26 g/l

Example 1.4

2-chloro-4-fluoro-5-nitrobenzoyl chloride (without catalyst)

22.3 g (0.1 mol) of 2-chloro-4-fluoro-5-nitrobenzoic acid
16.8 g (0.14 mol) of thionyl chloride
Yield: 47.0 g (95% of theory) of the title compound as a solution in chlorobenzene
Fluoride value: 0.02 g/l

Example 1.5

4-fluoro-5-nitrobenzoyl chloride (with DMAP)

18.5 g (0.1 mol) of 4-fluoro-5-nitrobenzoic acid
16.8 g (0.14 mol) of thionyl chloride
0.1 g (0.0008 mol) of 4-dimethylaminopyridine
Yield*: 40.8 g (96% of theory) of the title compound as a solution in chlorobenzene
Fluoride value: 0.03 g/l

Example 1.6

2-chloro-4-fluoro-5-nitrobenzoyl chloride (with DMAP)

22.3 g (0.1 mol) of 2-chloro-4-fluoro-5-nitrobenzoic acid
16.8 g (0.14 mol) of thionyl chloride
0.1 g (0.0008 mol) of 4-dimethylaminopyridine
Yield: 46.8 g (97% of theory) of the title compound as a solution in chlorobenzene
Fluoride value: 0.05 g/l

Example 1.7

4-fluoro-5-nitrobenzoyl chloride (with DMF)

18.5 g (0.1 mol) of 4-fluoro-5-nitrobenzoic acid
16.8 g (0.14 mol) of thionyl chloride
0.1 g (0.0014 mol) of dimethylformamide
Yield*: 40.8 g (98% of theory) of the title compound as a solution in chlorobenzene
Fluoride value: 0.02 g/l

Example 1.8

4-fluoro-5-nitrobenzoyl chloride (with pyridine)

18.5 g (0.1 mol) of 4-fluoro-5-nitrobenzoic acid
16.8 g (0.14 mol) of thionyl chloride
0.1 g (0.0013 mol) of pyridine
Yield*: 40.8 g (96% of theory) of the title compound as a solution in chlorobenzene
Fluoride value: 0.03 g/l

Example 1.9

2-chloro-4-fluoro-5-nitrobenzoyl chloride (with pyridine)

22.3 g (0.1 mol) 2-chloro-4-fluoro-5-nitrobenzoic acid
16.8 g (0.14 mol) of thionyl chloride
0.1 g (0.0013 mol) of pyridine
Yield: 46.8 g (98% of theory) of the title compound as a solution in chlorobenzene
Fluoride value: 0.13 g/l These experiments show that the process according to the invention distinctly reduces the fluoride elimination:

When the process is carried out according to known reaction conditions without catalyst or with catalysts such as DMAP, DMF or pyridine, there is elimination of fluoride which leads to a fluoride concentration of from 0.02 to 0.26 g/l, whereas the fluoride concentration when the reaction takes place under the inventive conditions is only 0.01 g/l.

Example 1.10

A mixture of 475 g (1.6 mol) of 2-chloro-4-fluoro-5-nitrobenzotrichloride and 1.5 g (9.1 mmol) of iron chloride was introduced and melted by heating to 75° C. Over the course of 2 h 29.2 g (1.6 mol) of water were metered in beneath the surface. In the course of the metered addition hydrogen chloride was produced, and was taken off via a suitable off-gas system. During the reaction the internal temperature rose slightly. After the end of the metered addition the system was stirred at 75° C. for 3 h. Residues of hydrogen chloride were driven off by introduction of nitrogen. The warm melt was transferred with stirring to a vessel containing 367 g of chlorobenzene which had been conditioned at 10° C. After cooling to approximately 20° C., this organic phase was extracted once with 300 g of 32% aqueous hydrochloric acid. Phase separation gave 732.0 g of a solution of 50.5% by weight (97% of theory) of 2-chloro-4-fluoro-5-nitrobenzoyl chloride in chlorobenzene. The free fluoride content of the organic phase was less than 0.01 g/1000 g (<10 ppm).

Example 1.11

A mixture of 296 g (1 mol) of 2-chloro-4-fluoro-5-nitrobenzotrichloride and 0.95 g (5.7 mmol) of iron chloride was introduced and melted by heating to 70° C. Over the course of 2 h 18.1 g (1 mol) of water were metered in beneath the surface. During the metered addition hydrogen chloride was formed, and was taken off via a suitable off-gas system. During the reaction there was a slight increase in the internal temperature. Toward the end of the metered addition a precipitate was formed which, at the end of the subsequent stirring time, had dissolved again. After the end of the metered addition, stirring was continued at 75° C. for 3 h. Residues of hydrogen chloride were driven off by introduction of nitrogen. The warm melt was cooled and solidified. This gave 235 g of 2-chloro-4-fluoro-5-nitrobenzoyl chloride with a purity of 97.5% (96% of theory).

Example 1.12

In the same way as example 1.11, 296 g (1 mol) of 2-chloro-4-fluoro-5-nitrobenzo-trichloride, 0.95 g (5.7 mmol) of iron chloride and 18.2 g (1 mol) of water were reacted at 80° C. This gave 238 g of 2-chloro-4-fluoro-5-nitrobenzoyl chloride with a purity of 97% (97% of theory).

Example 1.13

In the same way as in example 1.11, 296 g (1 mol) of 2-chloro-4-fluoro-5-nitrobenzo-trichloride, 0.5 g (3 mmol) of iron chloride and 18.2 g (1 mol) of water were reacted at 120° C. After the end of the metered addition of the water, stirring was continued for 30 minutes at 120-125° C. The system was subsequently cooled to 60° C. Residues of hydrogen chloride were driven off by introduction of nitrogen. The warm melt was cooled and solidified. This gave 236 g of 2-chloro-4- fluoro-5-nitrobenzoyl chloride with a purity of 95% (95% of theory). The free fluoride content was 0.110 g/1000 g (110 ppm).

Example 1.14

A mixture of 148 g (0.5 mol) of 2-chloro-4-fluoro-5-nitrobenzotrichloride and 0.5 g (3 mmol) of iron chloride was introduced and melted by heating to 85° C. Over the course of 1 h 111 g (1 mol) of 2-chloro-4-fluoro-5-nitrobenzoic acid in solid form were added. During the metered addition hydrogen chloride was formed, and was taken off via a suitable off-gas system. During the metered addition a precipitate formed. The temperature was raised to 120° C. and the mixture was stirred for 2 h. In the course of this stirring period the precipitate dissolved again. Residues of hydrogen chloride were driven off by introduction of nitrogen. The warm melt was cooled and solidified. This gave 2-chloro-4-fluoro-5-nitrobenzoyl chloride with a purity of 95% (94% of theory).

2. PREPARATION OF THE SULFONAMIDES I

Example 2.1

N-(2-chloro-4-fluoro-3-nitrobenzoyl)-N',N'-diethylsulfonamide

A mixture of 8.22 g (27.0 mmol) of N,N-diethylsulfamoylamide, 5.40 g (53.0 mmol) of triethylamine and 170 mg of lutidine were admixed in 40 g of chlorobenzene at 70° C. with 12.4 g (25.0 mol) of 2-chloro-4-fluoro-3-nitrobenzoyl chloride in 12 g of chlorobenzene. The reaction mixture was subsequently stirred at 70° C. for 2 h. The mixture was acidified by means of addition of conc. hydrochloric acid, cooled to 0° C. and stirred for 1 h.

The solid was filtered off and washed once with HCl solution. 6.7 g (73% of theory) of the title compound were obtained.

$^1$H NMR (500 MHz, CDCl$_3$) δ=9.30 ppm (br. s., NH), 8.45 (d, Ar—H), 7.45 (d, Ar—H), 3.5 [q, C$\underline{H}_2$CH$_3$], 1.30 (t, CH$_2$C$\underline{H}_3$).

Example 2.2

N-(4-fluoro-3-nitrobenzoyl)-N'-i-propyl-N'-methylsulfonamide 8.22 g (54.0 mol) of N-methyl-N-(1-methylethyl)sulfamoylamide, 36.0 mg (0.30 mmol) of dimethylaminopyridine (DMAP), 11.0 g (0.107 mmol) of triethylamine were admixed in 30 ml of toluene at 70° C. with 10.2 g (49.1 mmol) of 4-fluoro-3-nitrobenzoyl chloride in 30 ml of toluene. The suspension was subsequently stirred at RT for 2 h. The mixture was acidified by means of addition of conc. hydrochloric acid and stirred for 1 h. The solid was filtered off, washed once with 1N HCl solution and recrystallized from chlorobenzene. A final filtration and drying under reduced pressure gave rise to 14.3 g (87% of theory) of the title compound as yellowish crystals having a melting point of 164-165° C.

$^1$H NMR (500 MHz, d-DMSO) δ=12.3 ppm (br. s., NH), 8.85 (d, Ar—H), 8.40-8.45 (m, Ar—H), 7.75 (t, Ar—H), 4.25 [sept., C$\underline{H}$(CH$_3$)$_2$], 2.95 (s, CH$_3$), 1.15 ppm [d, CH(C$\underline{H}_3$)$_2$].

Example 2.3

N-(4-fluoro-3-nitrobenzoyl)-N'-i-propyl-N'-methylsulfonamide

A solution of 4.10 g (27.0 mmol) of N-methyl-N-(1-methylethyl)sulfamoylamide in 50 g of dioxane was admixed at 25° C. with 4.30 g (50% in water) of NaOH. During this addition, a solution of 5.32 g (25.0 mmol) of 4-fluoro-3-nitrobenzoyl chloride and 20 g of dioxane was added dropwise. The reaction mixture was subsequently stirred at 25° C. for 12 h. The mixture was diluted by means of addition of 140 g of water and acidified with conc. hydrochloric acid, cooled to 0° C. and stirred for 1 h. The solid was filtered off and washed once with HCl solution. 7.6 g (86% of theory) of the title compound having an m.p. of 164-165° C. were obtained.

Example 2.4

N-(2-chloro-4-fluoro-3-nitrobenzoyl)-N'-i-propyl-N'-methylsulfonamide

A solution of 41.1 g (0.27 mol) of N-methyl-N-(1-methylethyl)sulfamoylamide and 2.41 g (3.00 mmol) of tetrabutylammonium chloride in 500 g of tetrahydrofuran was admixed at 25° C. with 41.0 g (50% in water) of NaOH. During this addition, a solution of 59.7 g (0.25 mol) of 2-chloro-4-fluoro-3-nitrobenzoyl chloride and 65 g of tetrahydrofuran was added dropwise. The reaction mixture was subsequently stirred at 25° C. for 2 h and acidified by means of addition of conc. hydrochloric acid. This was followed by extraction with dichloromethane. The combined organic phases were dried over magnesium sulfate and the solvent was removed under reduced pressure. 67 g (76% of theory) of the title product having an m.p. of 125-127° C. were obtained.

$^1$H NMR (400 MHz, CDCl$_3$) δ=9.1 ppm (s, NH), 8.4 (d, Ar—H), 7.45 (d, Ar—H), 4.25 (sept., iPr-H), 2.95 (s, Me), 1.25 (d, iPr-H).

Example 2.5

N-(2-chloro-4-fluoro-3-nitrobenzoyl)-N'-i-propyl-N'-methylsulfonamide

A solution of 41.1 g (0.27 mol) of N-methyl-N-(1-methylethyl)sulfamoylamide and 0.75 g (1.25 mmol) of tributylmethylammonium chloride in 630 g of chlorobenzene was admixed at 20° C. with 41.0 g (50% in water) of NaOH. During this addition, a solution of 59.7 g (0.25 mol) of 2-chloro-4-fluoro-3-nitrobenzoyl chloride and 65 g of chlorobenzene was added dropwise. The biphasic reaction mixture was subsequently stirred at 20° C. for 1 h and then acidified by means of addition of conc. hydrochloric acid. Finally, the mixture was cooled to 0° C., and the precipitated solid was filtered off and washed with 1N HCl solution. 72.5 g (82% of theory) of the title compound were obtained.

$^1$H NMR (400 MHz, CDCl$_3$) δ=9.1 ppm (s, NH), 8.4 (d, Ar—H), 7.45 (d, Ar—H), 4.25 (sept., iPr-H), 2.95 (s, Me), 1.25 (d, iPr-H).

Example 2.6

A solution of 41.1 g (0.27 mol) of N-methyl-N-(1-methylethyl)sulfamoylamide and 0.75 g (12.0 mmol) of tributylmethylammonium chloride in 633 g of chlorobenzene was admixed at 20° C. with 41.0 g (50% in water) of NaOH over the course of 60 min. The addition of a solution of 59.7 g (0.25 mol) of 2-chloro-4-fluoro-3-nitrobenzoyl chloride and 62 g of chlorobenzene took place 15 min after the beginning of addition of the base, over the course of 45 min. The reaction mixture was subsequently stirred at 20° C. for 1 h and diluted by addition of 430 g of water. The aqueous phase was acidified to a pH of 1 using concentrated hydrochloric acid, and 320 g of cyclohexane were added. The mixture obtained was cooled to 0° C. The precipitate was isolated by filtration and dried at 70° C. under reduced pressure. This gave 80.1 g (88% of theory) of N-(2-chloro-4-fluoro-3-nitrobenzoyl)-N'-isopropyl-N'-methylsulfamide in a purity of 96%. The solid contained 2.2% of 2-chloro-4-fluoro-3-nitrobenzoic acid (determination via quantitative HPLC: column: Symmetry C18 5 μm 250×4.6 mm from Waters®; wavelength: 222 nm, 205 nm; eluent: gradient of A (0.1% by volume $H_3PO_4$ in $H_2O$) and B (0.1% by volume $H_3PO_4$ in $CH_3CN$); flow rate: 1 ml/min; pressure: about 150 bar).

Example 2.7

A solution of 43.1 g (0.277 mol) of N-methyl-N-(1-methylethyl)sulfamoylamide and 0.77 g (12.0 mmol) of tributylmethylammonium chloride in 640 g of chlorobenzene was admixed over the course of 60 min at 20° C. with 43.7 g (50% in water) of NaOH. After the base had been added for 15 minutes, a parallel addition commenced of 64.0 g (0.26 mol) of 2-chloro-4-fluoro-3-nitrobenzoyl chloride in 67 g of chlorobenzene. This addition took place over the course of 45 min. The reaction mixture was subsequently stirred at 20° C. for 1 h and diluted by addition of 424 g of water and 138 g of isohexane. The aqueous phase was acidified to a pH of 5.5 using concentrated hydrochloric acid and then separated off at 68° C. The organic phase was extracted a second time with addition of 430 g of water and 60 g of isohexane, and the phases were separated at 68° C. The resulting organic phase was admixed with a further 280 g of isohexane and then cooled to 0° C. Filtration, washing with water and drying under reduced pressure at 70° C. gave 82.4 g (87% of theory, purity 96.5%) of N-(2-chloro-4-fluoro-3-nitrobenzoyl)-N'-isopropyl-N'-methylsulfamide.

Example 2.8

A solution of 43.1 g (0.277 mol) of N-methyl-N-(1-methylethyl)sulfamoylamide and 0.77 g (12.0 mmol) of tributylmethylammonium chloride in 637 g of chlorobenzene was admixed over the course of 60 min at 20° C. with 43.7 g (50% in water) of NaOH. After the base had been added for 15 minutes, a parallel addition commenced of 65.0 g (0.26 mol) of 2-chloro-4-fluoro-3-nitrobenzoyl chloride in 70 g of chlorobenzene. This addition took place over the course of 45 min. The reaction mixture was subsequently stirred at 20° C. for 1 h and diluted by addition of 424 g of water and 138 g of isohexane. The aqueous phase was acidified to a pH of 4.5 using concentrated hydrochloric acid and then separated off at 68° C. The organic phase was extracted a second time with addition of 430 g of water and 60 g of isohexane, and the phases were separated at 68° C. The resulting organic phase was admixed with a further 280 g of isohexane and then cooled to 0° C. Filtration, washing with water and drying under reduced pressure at 70° C. gave 82.1 g (87% of theory, purity 97%) of N-(2-chloro-4-fluoro-3-nitrobenzoyl)-N'-isopropyl-N'-methylsulfamide. In the solid, HPLC analysis found no contamination with 2-chloro-4-fluoro-3-nitrobenzoic acid.

Example 2.9

A solution of 8.22 g (54.0 mmol) of N-methyl-N-(1-methylethyl)sulfamoylamide in 25 g of water and 6.48 g (162.4 mmol) of NaOH was admixed with 1.74 g (5.40 mmol) of tetrabutylammonium bromide (TBAB) and 10 g of chlorobenzene. Subsequently, at 25° C., a solution of 10.49 g (48.6 mmol) of 4-fluoro-3-nitrobenzoyl chloride and 25 g of chlorobenzene was added dropwise over 40 min. The two-phase reaction mixture was subsequently stirred at 25° C. for 3 h. Following phase separation, the organic phase was dried over magnesium sulfate and the solvent was removed under reduced pressure. This gave 4.56 g (46.2%) of N-(4-fluoro-3-nitrobenzoyl)-N'-isopropyl-N'-methylsulfamide having an m.p. of 164-165° C.

Example 2.10

A solution of 10.5 g (69.0 mmol) of N-methyl-N-(1-methylethyl)sulfamoylamide, 190.0 mg (0.80 mmol) of tributylmethylammonium chloride in 160 g of chlorobenzene, and 0.86 g of water was admixed with 10.9 g (137.0 mmol, 50%) of NaOH. Subsequently at 20° C. a solution of 15.8 g (66.0 mmol) of 2-chloro-4-fluoro-3-nitrobenzoyl chloride and 16 g of chlorobenzene was added dropwise in 65 min. The two-phase reaction mixture was subsequently stirred overnight at 20° C. The reaction mixture was diluted with 106 g of water and acidified to a pH of 1 with sulfuric acid (98% strength). Following phase separation, the organic phase was cooled to 0° C. and filtered. The resulting solid was washed on the filter with dilute sulfuric acid (pH 1) and finally dried at 70° C. under reduced pressure. This gave 9.3 g (37.3% of theory) of N-(2-chloro-4-fluoro-3-nitrobenzoyl)-N'-isopropyl-N'-methylsulfamide. Additionally an organic phase was obtained that contained 6.08 g (24.4% of theory) of N-(2-chloro-4-fluoro-3-nitrobenzoyl)-N'-isopropyl-N'-methylsulfamide and also 3.29 g (22.5% of theory) of 2-chloro-4-fluoro-3-nitrobenzoic acid (determination by quantitative HPLC in the same way as in ex. 2.3).

3. PREPARATION OF THE ANILINE DERIVATIVES VI

Example 3.1

N—(N-(4-Fluoro-3-aminobenzoyl)-N'-isopropyl-N'-methylsulfamide 89.0 g (0.28 mol) of N-(4-fluoro-3-nitrobenzoyl)-N'-isopropyl-N'-methylsulfamide in methanol were admixed with 5.9 g (10 mol %) of Pd/C and hydrogenated with 2-5 bar of hydrogen with stirring at 25-30° C. After 12 h the solution was depressurized, the reaction mixture was filtered and the solvent was removed by distillation. This gave 80.1 g (98%) of the title compound in the form of a beige solid (m.p.: 148-150° C.).

In addition to the implementation described above, table 1 lists further experiments carried out in the same way as the above process:

TABLE 1

| No. | Catalyst system | mol % | p $H_2$ [bar] | T [° C.] | t [h] | Solvent | Yield [%] |
| --- | --- | --- | --- | --- | --- | --- | --- |
| 1 | 10% Pd/C | 0.91 | 5 | 26 | 12 | methanol | 98 |
| 2 | 10% Pd/C | 0.23 | 5 | 26 | 9 | methanol | 98 |
| 3 | 3% Pt/C | 0.49 | 5 | 26 | 9 | methanol | 95 |

TABLE 1-continued

| No. | Catalyst system | mol % | p H$_2$ [bar] | T [° C.] | t [h] | Solvent | Yield [%] |
|---|---|---|---|---|---|---|---|
| 4 | 5% Ir/C | 0.49 | 5 | 26 | 9 | methanol | 74 |
| 5 | 5% Ru/C | 0.49 | 5 | 26 | 9 | methanol | 78 |
| 6 | 5% Pt/C | 0.52 | 5 | 26 | 9 | methanol | 95 |
| 7 | 1% Pt/0.1% Cu/C | 0.51 | 5 | 26 | 9 | methanol | 99 |
| 8 | 10% Pd/C | 0.94 | 5 | 26 | 9 | toluene/methanol 1:1 | 96 |
| 9 | 5% Pd/0.1% Pt/0.1% Fe/C | 0.24 | 5 | 26 | 9 | methanol | 55 |
| 10 | 1% Pt/2% V/C | 0.24 | 5 | 26 | 9 | toluene | 98 |
| 11 | 1% Pt/0.2% Ni/C | 0.23 | 5 | 26 | 9 | toluene | 79 |
| 12 | 10% Pd/C | 0.29 | 5 | 26 | 9 | chlorobenzene/methanol 1:1 | 97 |
| 13 | 10% Pd/C | 0.6 | 5 | 26 | 12 | n-butyl acetate | 99 |
| 14 | 10% Pd/C | 0.91 | 5 | 26 | 12 | dichloromethane | 92 |
| 15 | 5-10% Pd/C | 0.26 | 5 | 26 | 9 | chlorobenzene | 87 |
| 16 | 10% Pd/C | 0.26 | 5 | 26 | 12 | ethyl acetate | 77 |
| 17 | 1% Pt/0.1% Cu/C | 0.25 | 5 | 26 | 9 | chlorobenzene | 98 |
| 18 | 1% Pt/2% V/C | 0.25 | 5 | 26 | 9 | chlorobenzene | 96 |
| 19 | 10% Pd/C | 0.30 | 5 | 26 | 12 | tetrahydrofuran | 87 |
| 20 | 10% Pd/C | 0.26 | 5 | 26 | 12 | ethyl acetate/methanol 1:1 | 97 |
| 21 | 1% Pt/2% V/C | 0.50 | 5 | 26 | 9 | methanol | 94 |
| 22 | 10% Pd/C | 0.11 | 5 | 26 | 9 | methanol | 64 |
| 23 | 1% Pt/0.1% Cu/C | 0.24 | 5 | 26 | 9 | toluene | 89 |
| 24 | 10% Pd/C | 0.50 | 2 | 26 | 9 | methanol | 97 |
| 25 | 10% Pd/C | 0.15 | 2 | 26 | 9 | methanol | 96 |
| 26 | 1% Pt/2% V/C | 0.24 | 5 | 50 | 9 | chlorobenzene | 77 |
| 27 | 5% Pt/C | 0.25 | 5 | 30 | 9 | chlorobenzene/methanol 7:1 | 97 |
| 28 | 5% Pt/C | 0.26 | 5 | 50 | 9 | chlorobenzene | 96 |
| 29 | 1% Pt/0.1% Cu/C | 0.25 | 5 | 50 | 9 | chlorobenzene | 93 |
| 30 | 10% Pd/C | 0.51 | 2 | 50 | 9 | methanol | 97 |
| 31 | 10% Pd/C | 0.51 | 5 | 70 | 9 | chlorobenzene | 98 |

Example 3.2

N—(N-(2-Chloro-4-fluoro-3-aminobenzoyl)-N'-isopropyl-N'-methylsulfamide 8.00 g (23.0 mmol) of N-(2-chloro-4-fluoro-3-nitrobenzoyl)-N'-isopropyl-N'-methylsulfamide in 33 g of toluene and 8 g of methanol were admixed with 190 mg (0.055 mol %) of 3% Pt/C and hydrogenated with 5 bar of hydrogen with stirring at 70° C. After 12 h the solution was depressurized, the reaction mixture was filtered and the solvent was removed by distillation. This gave 4.7 g (64%) of the title compound in the form of a solid (m.p.: 147-149° C.).

Example 3.3

N—(N-(2-Chloro-4-fluoro-3-aminobenzoyl)-N'-isopropyl-N'-methylsulfamide 8.00 g (0.023 mol) of N-(2-chloro-4-fluoro-3-nitrobenzoyl)-N'-isopropyl-N'-methylsulfamide and 70 mg (6 mol %) of ammonium chloride in 33 g of toluene and 8 g of methanol were admixed with 0.19 g (0.15 mol %) of 10% Pd/C and hydrogenated with 5 bar of hydrogen with stirring at 70° C. After 10 h the solution was depressurized, the reaction mixture was filtered and the solvent was removed by distillation. This gave 6.4 g (89%) of the title compound in the form of a solid (m.p.: 147-149° C.).

Example 3.4

N—(N-(2-Chloro-4-fluoro-3-aminobenzoyl)-N'-isopropyl-N'-methylsulfamide 182.4 g (0.500 mol) of N-(2-chloro-4-fluoro-3-nitrobenzoyl)-N'-isopropyl-N'-methylsulfamide in 391 g of methanol were admixed with 1.33 g (0.005 mol %) of 1% Pt-2% V/C and hydrogenated with 5 bar of hydrogen with stirring at 60° C. After 6 h the solution was depressurized, the reaction mixture was filtered and the solvent was removed by distillation. This gave 157.1 g (97%) of the title compound in the form of a solid (m.p.: 147-149° C.).

Example 3.5

N—(N-(2-Chloro-4-fluoro-3-aminobenzoyl)-N'-isopropyl-N'-methylsulfamide 8.00 g (0.023 mol) of N-(2-chloro-4-fluoro-3-nitrobenzoyl)-N'-isopropyl-N'-methylsulfamide in 75 g of toluene and 8 g of methanol were admixed with 0.24 g (0.05 mol %) of 2.4% Pt/2.4% Pd/C and hydrogenated with 5 bar of hydrogen with stirring at 70° C. After 11 h the solution was depressurized, the reaction mixture was filtered and the solvent was removed by distillation. This gave 6.48 g (90%) of the title compound in the form of a solid (m.p.: 147-149° C.).

What is claimed is:

1. A process for preparing a sulfonamide of formula I

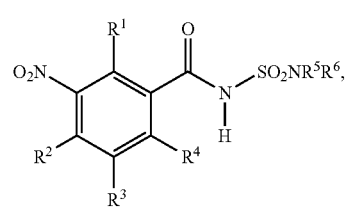

wherein:

$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;

$R^5$ and $R^6$ are each $C_1$-$C_6$-alkyl;

by reacting a m-nitrobenzoyl chloride of formula II

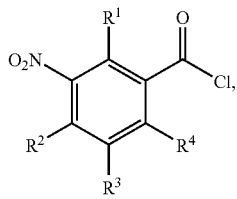

II wherein the variables $R^1$, $R^2$, $R^3$ and $R^4$ are each as defined above:

with an amino sulfone of formula III

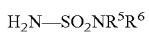 III, wherein the variables $R^5$ and $R^6$ are each as defined above;

under the influence of B equivalents of alkali metal or alkaline earth metal hydroxide as base, wherein, in a first step, the amino sulfone of formula III is reacted with B1 equivalents of alkali metal or alkaline earth metal hydroxide, and, in a second step, the reaction mixture resulting from the first step is reacted with m-nitrobenzoyl chloride of formula II and B2 equivalents of alkali metal or alkaline earth metal hydroxide;

wherein

B is 1.5-3 equivalents of alkali metal or alkaline earth metal hydroxide with respect to the amino sulfone of formula III;

B1 is a subportion of B and is in the range from 0.1-1.3 equivalents of alkali metal or alkaline earth metal hydroxide with respect to the amino sulfone of formula III; and B2 is a subportion of B and is the difference between B and B1.

2. The process of claim 1, wherein B is 1.8-2.5 equivalents of alkali metal or alkaline earth metal hydroxide with respect to the amino sulfone III.

3. The process of claim 2, wherein, in the first step, the amino sulfone is introduced as an initial charge in an inert solvent and then B1 equivalents of alkali metal or alkaline earth metal hydroxide are added.

4. The process of claim 3, wherein B1 is 0.1-1 equivalent of alkali metal or alkaline earth metal hydroxide with respect to the amino sulfone of formula III.

5. The process of claim 4, wherein, in the first step, the m-nitrobenzoyl chloride of formula II and the B2 equivalents of alkali metal or alkaline earth metal hydroxide are added simultaneously to the reaction mixture resulting from the first step.

6. The process of claim 5, wherein the reaction is carried out in an aqueous multiphase system.

7. The process of claim 6, wherein the m-nitrobenzoyl chloride of formula II is prepared by reacting a m-nitrobenzoic acid of formula VII

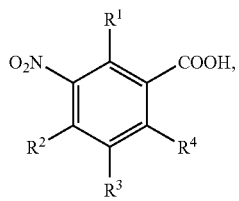

VII wherein:

$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;

with a chlorinating agent; or by hydrolyzing corresponding benzotrichloride of formula X

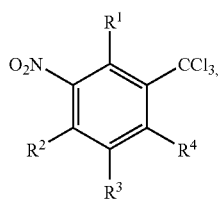

X wherein:

$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;

in the presence of a catalyst or in a weakly acidic medium; or by reacting corresponding benzotrichloride of formula X with a m-nitrobenzoic acid of formula VII in the presence of a catalyst.

8. The process of claim 6, wherein the m-nitrobenzoyl chloride of formula II is prepared by reacting a m-nitrobenzoic acid of formula VII

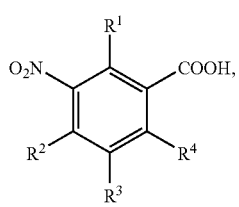

VII wherein:

$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;

with a chlorinating agent.

9. The process of claim 6, wherein the m-nitrobenzoyl chloride of formula II is prepared by hydrolyzing corresponding benzotrichloride X

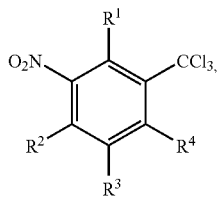

wherein:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
in the presence of a catalyst or in a weakly acidic medium.

10. The process of claim 6, wherein the m-nitrobenzoyl chloride II is prepared by reacting corresponding benzotrichloride X

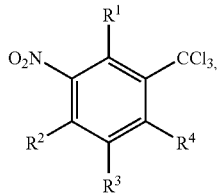

wherein:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
with a m-nitrobenzoic acid VII

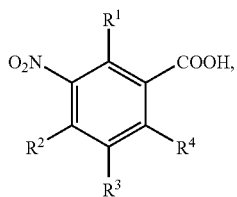

wherein:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
in the presence of a catalyst.

11. A process for preparing aniline derivatives VI

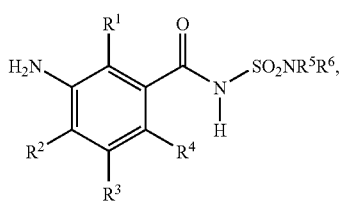

wherein:
$R^1$, $R^2$, $R^3$ and $R^4$ are each hydrogen, halogen, cyano, nitro, $C_1$-$C_6$-alkyl, $C_1$-$C_6$-haloalkyl, $C_1$-$C_6$-alkoxy or $C_1$-$C_6$-haloalkoxy;
$R^5$ and $R^6$ are $C_1$-$C_6$-alkyl, by reducing a sulfonamide of formula I,

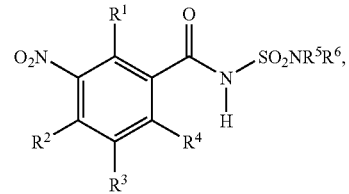

wherein the sulfonamide has been prepared according to claim 1.

12. The process of claim 11, wherein the reduction is carried out with hydrogen in the presence of catalytic amounts of a transition metal catalyst.

13. The method of claim 1, wherein the compound of formula II is prepared by reacting a compound of formula VIIA

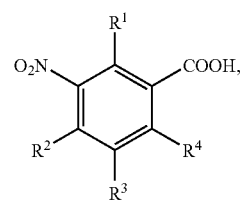

with a chlorinating agent,
wherein the reaction takes place in the presence of catalytic amounts of a phosphine derivative IX

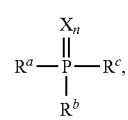

wherein:
$R^a$, $R^b$, $R^c$ are each $C_1$-$C_6$-alkyl or phenyl, which may optionally be substituted by $C_1$-$C_4$-alkyl;
X is oxygen or two single-bonded chlorine atoms;
n is 0 or 1.

14. The process according to claim 13, wherein
$R^1$ is hydrogen;
$R^2$ is hydrogen or halogen;
$R^3$ is hydrogen; and
$R^4$ is hydrogen or halogen;
wherein at least one of the $R^2$ and $R^4$ radicals is fluorine.

15. The process according to claim 13, wherein the chlorinating agent is selected from the group consisting of oxalyl chloride, phosphorus trichloride, phosphorus pentachloride, thionyl chloride and phosphoryl chloride ($POCl_3$).

16. The process of claim 15, wherein the ratio of the chlorinating agent to the compound of formula VIIA is 1.5 to 1.

17. The process of claim 16, wherein the phosphine derivative IX is selected from the group consisting of triphenylphosphine, triphenylphosphine oxide and tri($C_1$-$C_6$-alkyl)phosphine oxide.

18. The process of claim 13, wherein the reaction is effected additionally in the presence of a Lewis acid.

19. The process of claim 18, wherein the Lewis acid is selected from the group consisting of boric acid, tri-$C_1$-$C_4$-alkyl borate and cyclic boric esters.

* * * * *